US009540425B2

(12) United States Patent
Ndam et al.

(10) Patent No.: US 9,540,425 B2
(45) Date of Patent: Jan. 10, 2017

(54) VACCINES AGAINST PREGNANCY-ASSOCIATED MALARIA

(75) Inventors: Nicaise Tuikue Ndam, Paris (FR); Philippe Deloron, Paris (FR); Sedami Ursula Alix Carine Gnidéhou, Tavemy (FR); Mickaël Quiviger, Le Grand Quevilly (FR); Pascal Bigey, Paris (FR); Daniel Scherman, Paris (FR)

(73) Assignee: INSTITUT DE RECHERCHE POUR LE DéVELOPPEMENT (IRD), Marseilles (FR)

( * ) Notice: Subject to any disclaimer, the term of this patent is extended or adjusted under 35 U.S.C. 154(b) by 0 days.

(21) Appl. No.: 13/812,197

(22) PCT Filed: Jul. 29, 2011

(86) PCT No.: PCT/IB2011/002069
§ 371 (c)(1),
(2), (4) Date: Jan. 25, 2013

(87) PCT Pub. No.: WO2012/014073
PCT Pub. Date: Feb. 2, 2012

(65) Prior Publication Data
US 2013/0129767 A1     May 23, 2013

(30) Foreign Application Priority Data

Jul. 30, 2010  (FR) ...................... 10 56294

(51) Int. Cl.
*A61K 39/015*  (2006.01)
*A61K 39/00*   (2006.01)
*C07K 14/445*  (2006.01)

(52) U.S. Cl.
CPC ............. *C07K 14/445* (2013.01); *A61K 39/00* (2013.01); *A61K 39/015* (2013.01); *A61K 2039/53* (2013.01)

(58) Field of Classification Search
None
See application file for complete search history.

(56) References Cited

U.S. PATENT DOCUMENTS

2007/0053928 A1    3/2007  Theander et al.
2009/0130136 A1*   5/2009  Miller et al. ............... 424/192.1

FOREIGN PATENT DOCUMENTS

WO    WO-2004/067559 A1    8/2004

OTHER PUBLICATIONS

Singh et al. *Nature Struct. Mol. Biol.* 15: 932-938, 2008.*
Avril et al., "Evidence for Globally Shared, Cross-Reacting Polymorphic Epitopes in the Pregnancy-Associated Malaria Vaccine Candidate VAR2CSA," *Infection and Immunity*, 76: 1791-1800 (2008).
Bigey et al., "The NTS-DBL2X Region of VAR2CSA Induces Cross-Reactive Antibodies That Inhibit Adhesion of Several *Plasmodium falciparum* Isolates to Chondroitin Sulfate A," *Journal of Infectious Diseases*, 204: 1125-1133 (2011).
Bordbar et al., "Identification of Id1-DBL2X of VER2CSA as a Key Domain Inducing Highly Inhibitory and Cross-Reactive Antibodies," *Vaccine*, 30: 1343-1348 (2012).
Dahlback et al., "Can Any Lessons be Learned From the Ambiguous Glycan Binding of PfEMP1 Domains?," *Trends in Parasitology*, 26: 230-235 (2010).
Dahlbäck et al., "The Chondroitin Sulfate A-binding Site of the VAR2CSA Protein Involves Multiple N-Terminal Domains," *The Jo. Bio. Chem.*, 286: 15908-15917 (2011).
Hill et al., "Prime-Boost Vectored Malaria Vaccines: Progress and Prospects," *Human Vaccines*, 6: 78-83 (2010).
Khunrae et al., "Full-Length Recombinant *Plasmodium falciparum* VAR2CSA Binds Specifically to CSPG and Induces Potent Parasite Adhesion-Blocking Antibodies," *J. Mol. Biol.*, 397: 826-834 (2010).
Nielsen et al., "Induction of Adhesion-Inhibitory Antibodies Against Placental *Plasmodium falciparum* Parasites by Using Single Domains of VAR2CSA," *Infection and Immunity*, 77: 2482-2487 (2009).
Pinto et al., "Differential Induction of Functional IgG Using the *Plasmodium falciparum* Placental Malaria Vaccine Candidate VAR2CSA," *PLoS One*, 6: e17942 (2011).
Salanti et al., "Several Domains From VAR2CSA Can Induce *Plasmodium falciparum* Adhesion-Blocking Antibodies," 9: 11 (2010).
Srivastava et al., "Var2CSA Minimal CSA Binding Region is Located Within the N-Terminal Region," PLoS One, 6: e20270 (2011).
International Search Report for International application No. PCT/IB2011/002069, dated Feb. 3, 2012.
Search Report for French Application No. FR 1056294, dated May 16, 2011.
Written Opinion for International application No. PCT/IB2011/002069, dated Feb. 3, 2012.

* cited by examiner

*Primary Examiner* — S. Devi
(74) *Attorney, Agent, or Firm* — Marshall, Gerstein & Borun LLP

(57) ABSTRACT

The present invention relates to specific regions of the N-terminal portion of the VAR2CSA protein and to the use of such specific regions in the prevention of pregnancy-associated malaria. The invention also provides immunogenic compositions and vaccines that are useful for preventing malaria in pregnant women.

10 Claims, 8 Drawing Sheets a: BSA
b: IgGs in prebleed
c: IgGs post NTS-DBL2x immunization
d: IgGs post DBL6ε immunization
e: CSA 500 μg/mL

VACCINES AGAINST PREGNANCY-ASSOCIATED MALARIA

RELATED PATENT APPLICATIONS

The present application is filed pursuant to 35 U.S.C. §371 as a U.S. National Phase Application of International Patent Application No. PCT/IB2011/002069, which was filed on Jul. 29, 2011, claiming the benefit of priority to French Patent Application number FR 10 56294 filed on Jul. 30, 2010. The content of each of the aforementioned Patent Applications is incorporated herein by reference in its entirety.

FIELD OF THE INVENTION

The present invention relates to the use of specific regions of the N-terminal portion of the VAR2CSA protein in the prevention or treatment of pregnancy-associated malaria.

BACKGROUND OF THE INVENTION

Malaria is the most frequent parasitic infectious disease in the world. It is caused by a eukaryotic microorganism of the *Plasmodium* genus which is transmitted through biting by a female mosquito (*Anopheles*). Several species of *Plasmodium* can infect human beings, but *Plasmodium falciparum* is the most frequent and most pathogenic species and the species that is responsible for deadly cases. Once introduced in the blood, the parasite infects hepatic cells, in which it proliferates, before circulating again in the blood and invading red blood cells (erythrocytes). Malaria affects about a hundred countries in the world, in particular poor tropical regions of Africa, Asia and South America, Africa being by far the most affected continent. The World Health Organization estimates that malaria is responsible for 225 millions of cases of fever and approximately one million deaths annually (World Malaria Report, WHO, 2010). Currently available means of fighting against malaria infection include anti-malaria drugs (in particular chloroquine and quinine) and action against mosquitoes, vectors of the parasite. However, the situation is all the more worrisome that for several years, the parasites have developed increased resistance to drugs and mosquitoes have developed resistance to insecticide. Today, there are no vaccines available against malaria.

Malaria affects mainly children of less than 5 years of age and pregnant women, in particular primigravidae (i.e., women who are pregnant for the first time). Pregnant women are particularly vulnerable because the placenta constitutes a target where parasites can accumulate. In pregnant women, malaria infection can cause a large variety of damaging effects: spontaneous abortion, early delivery, low weight at birth, congenital transmission, and neonatal death. In the African regions where malaria is endemic, 3 to 5% of newborn deaths can be imputed to pregnancy-associated malaria. Furthermore, it is also a real danger for the mother who can suffer from sometimes severe, or even deadly, anaemia.

Today prevention of malaria in pregnant women is achieved by preventive administration of sulfadoxine/pyrimethamine (Cot et al., Br. Med. Bull., 2003, 67: 137-148). However, this intermittent treatment cannot provide a prevention against malaria during the entire pregnancy; firstly because administration of the drugs only takes place from the 20$^{th}$ week of pregnancy (the teratogenic risks during embryogenesis being too high); secondly because the treatment involves two curative doses of sulfadoxine/pyrimethamine administered at one month interval, which only provides partial medicinal protection; and thirdly because the efficacy of sulfadoxine/pyrimethamine is very strongly decreasing in all malaria endemic zones due to a rise in parasite resistance (Cot et al., Am. J. Trop. Med. Hyg., 1998, 59: 813-822; WHO/HTM/MAL/2005.1103. Geneva: World Health Organization; ter Kuile et al., JAMA, 2007, 297: 2603-2616; Mockenhaupt et al., J. Infect. Dis., 2008, 198: 1545-1549; Briand et al., J. Infect. Dis., 2009, 991-1001; Harrington et al., Proc. Natl. Acad. Sci. USA, 2009, 106: 9027-9032). Drugs are currently tested in this context, and numerous efforts are focused toward the development of a vaccine against placental malaria. The possibility of vaccinating pregnant women or prepubertal girls would offer several obvious advantages over the sulfadoxine/pyrimethamine treatment, since the preventive protection would be temporally extended, and probably of higher quality.

One of the contemplated vaccinal strategies to fight against pregnancy-associated malaria is to re-create the natural protective immunity. Indeed, the clinical severity of malaria caused by *Plasmodium falciparum* is, at least partly, linked to alterations undergone by infected erythrocytes. These alterations are induced by proteins of the parasite that are exported to the surface of erythrocytes during the phase of development in blood. Some of these surface proteins of the PfEMP1 (*Plasmodium falciparum* Erythrocyte Membrane Protein 1) family, confer novel cytoadherence properties to infected erythrocytes. The infected erythrocytes bind to the internal walls of blood vessels, thereby becoming unavailable for transport towards purging organs of the immune system, whose role is to destroy cells recognized as abnormal. In pregnancy-associated malaria, infected erythrocytes adhere to chondroitin sulfate A (CSA), a sulfated glycosaminoglycan present in the placenta. After several pregnancies, women acquire protective antibodies that block this adherence. One vaccinal strategy is to re-create this protective immunity by blocking the attachment of infected erythrocytes to the placenta.

The VAR2CSA protein, one of the members of the PfEMP1 family, is currently the object of numerous research projects with the goal of developing a vaccine specifically adapted to pregnant women (Tuikue Ndam et al., J. Infect. Dis., 2005, 192: 331-335; Chia et al., J. Infect. Dis., 2005, 192: 1284-1293; Tuikue Ndam et al., J. Infect. Dis., 2006, 193: 713-720; Dahlback et al., PLoS Pathogens, 2006, 2: 1069-1082; Badaut et al., Mol. Biochem. Parasitol., 2007, 15: 89-99; Khattab et al., Parasitol. Res., 2007, 101: 767-774; Guitard et al., Malaria J., 2008, 11: 7-10; Guitard et al., Malaria J., 2010, 9: 165; Gangnard et al., Mol. Biochem. Parasitol., 2010, 173: 115-122; Gnidehou et al., Mol. Biochem. Parasitol., 2010, 5(10): e13105). Although these studies are rendered difficult by VAR2CSA polymorphism, Phase I trials are nevertheless contemplated. Furthermore, the full-length extracellular domain of this protein has recently been expressed in a heterologous system (Srivastava et al., Proc. Natl. Acad. Sci. USA, 2010, 107: 4884-4889; Khunrae et al., J. Mol. Biol., 2010, 397: 826-834), and antibodies induced against this construct showed a very high anti-adhesion IgG titer. However, technological constraints in the optimal production of such a large antigen question the use of full length VAR2CSA in vaccine development. Furthermore, the development of new vaccinal approaches will have to take into account the numerous immunodominant epitopes that do no induce "antiadherent" antibodies.

Therefore, it appears to be crucial to continue exploring and developing new strategies to fight and prevent pregnancy-associated malaria.

SUMMARY OF THE INVENTION

In their study of the modulation of the immune response to *Plasmodium falciparum* during pregnancy, the present inventors have generated overlapping fragments of the sequence of the var2csa gene from the FCR3 parasite strain, introduced these fragments into plasmids, and intramuscularly injected each of the plasmids obtained in mice and in rabbits. They have identified the N-terminal portion of VAR2CSA, and more specifically the sub-region consisting in the DBL1x domain, the Id1 inter-domain and the DBL2x domain (i.e., NTS-DBL1x-Id1-DBL2x), as being the region of VAR2CSA that contains epitopes capable of inducing in vivo production of antibodies that block the binding of *Plasmodium falciparum*-infected erythrocytes to CSA. They then produced a recombinant protein corresponding to that particular portion of VAR2CSA and confirmed, via protein vaccination, the observations made with genetic vaccination. Further results have allowed the Id1-DBL2x region of the VAR2CSA protein to be identified as the minimal antigenic region of VAR2CSA that is involved in the acquisition of protective immunity against placental sequestration taking place during pregnancy-associated malaria.

Consequently, in a first aspect, the present invention relates to the use of polypeptides corresponding to and polynucleotides encoding specific regions of the N-terminal portion of the VAR2CSA protein in the fight against placental malaria.

More specifically, the present invention provides an isolated or purified polypeptide consisting of the NTS-DBL1x-Id1-DBL2x region of the VAR2CSA protein, or a biologically active fragment of the NTS-DBL1x-Id1-DBL2x region, for the treatment or prevention of pregnancy-associated malaria, wherein the biologically active fragment comprises at least the Id1-DBL2x region of the VAR2CSA protein.

In certain embodiments, the NTS-DBL1x-Id1-DBL2x region has the sequence set forth in SEQ ID NO: 1, or a homologous sequence thereof.

In certain embodiments, the Id1-DBL2x has the sequence set forth in SEQ ID NO: 2, or a homologous sequence thereof.

In certain embodiments, the isolated or purified polypeptide consists of the Id1-DBL2x region of the VAR2CSA protein.

The invention also provides a fusion protein for use in the treatment or prevention of pregnancy-associated malaria. A fusion protein according to the invention consists of a polypeptide as described herein fused to a fusion partner selected from the group consisting of maltose binding protein, signal sequence of the maltose binding protein, polyhistidine tag, S-Tag, glutathione-S-transferase, thioredoxin, β-galactosidase, streptavidin, dihydrofolate reductase, pelB signal sequence, ompA signal sequence, signal sequence of alkaline phosphatase, green fluorescent protein (GFP), toxins, human growth hormone, interleukin-2 (IL-2), granulocyte macrophage colony stimulating factor (GM-CSF), granulocyte colony stimulating factor (G-CSF), calcitonin, interferon-beta, interferon-alpha, glucagon like peptide 1 (GLP-1), glucagon like peptide 2 (GLP-2), PA toxin, parathyroid hormone (PTH(1-34) and PTH(1-84)), butyrylcholinesterase, glucocerebrosidase (GBA), and exendin-4.

The present invention also provides an isolated or purified polynucleotide for use in the treatment or prevention of pregnancy-associated malaria, the polynucleotide consisting of a sequence encoding a polypeptide or a fusion protein according to the invention and elements necessary to the in vitro or in vivo expression of said polypeptide or fusion protein.

In another aspect, the present invention provides a cloning or expression vector comprising at least one polynucleotide described above. Cloning or expression vectors according to the invention allow the expression, in host cells of a polypeptide consisting of the NTS-DBL1x-Id1-DBL2x region of the VAR2CSA protein, or a biologically active fragment thereof comprising at least the Id1-DBL2x region of VAR2CSA. These vectors may be phages, plasmids, cosmids, or viruses. The NTS-DBL1x-Id1-DBL2x region, or biologically active fragment thereof, may be fused to a fusion partner has described herein.

The invention also provides host cells (transformed or transfected) comprising at least on polynucleotide or at least one vector as described above. The host cells may be bacteria, yeast, insect cells or mammal cells.

In another aspect, the invention provides an immunogenic composition comprising at least one pharmaceutically acceptable excipient or carrier and at least one member of the group consisting of polypeptides according to the invention, fusion proteins according to the invention, polynucleotides according to the invention, and vectors according to the invention. Preferably, such an immunogenic composition can induce antibodies that prevent adherence of *Plasmodium falciparum*-infected erythrocytes to the placenta receptor CSA.

In a related aspect, the invention relates to vaccines against pregnancy-associated malaria. More specifically, the invention provides a DNA vaccine comprising a DNA, naked or formulated, comprising and expressing in vivo, a nucleotide sequence encoding a polypeptide consisting of the NTS-DBL1x-Id1-DBL2x region of the VAR2CSA protein, or a biologically active fragment thereof, fused or not to one or more fusion partners, as described herein. The invention also provides a protein vaccine comprising a polypeptide or a fusion protein of the invention. Preferably, the vaccines according to the present invention induce antibodies that prevent *Plasmodium falciparum*-infected erythrocytes from attaching to the placenta receptor CSA. Vaccines according to the invention may further comprise an adjuvant.

In a related aspect, the invention relates to methods of treatment or prevention of pregnancy-associated malaria. More specifically, the invention provides a method for inducing a protective immune response against *Plasmodium falciparum* in a female human being, the method comprising a step of administering an effective amount of an immunogenic composition or vaccine according to the invention. The invention also provides a method of vaccinating a female human being against *Plasmodium falciparum*, the method comprising a step of administering an effective amount of a vaccine of the invention, in particular a DNA vaccine or a protein vaccine described herein. The methods of treatment or prevention of pregnancy-associated malaria are mainly intended to women in age of bearing children (in particular postpubertal girls and primigravidae women) and to prepubertal girls. In certain preferred embodiments, a method of treatment or prevention of pregnancy-associated malaria induces, in the female human being treated, the production of antibodies that prevent *Plasmodium falciparum*-infected erythrocytes from attaching to the placenta receptor CSA. In the methods of treatment or prevention pregnancy-associated malaria according to the invention, the immunogenic composition or vaccine may be administered by any suitable route.

These and other objects, advantages and features of the present invention will become apparent to those of ordinary skill in the art having read the following detailed description of the preferred embodiments.

DETAILED DESCRIPTION OF CERTAIN PREFERRED EMBODIMENTS

Figure 1:
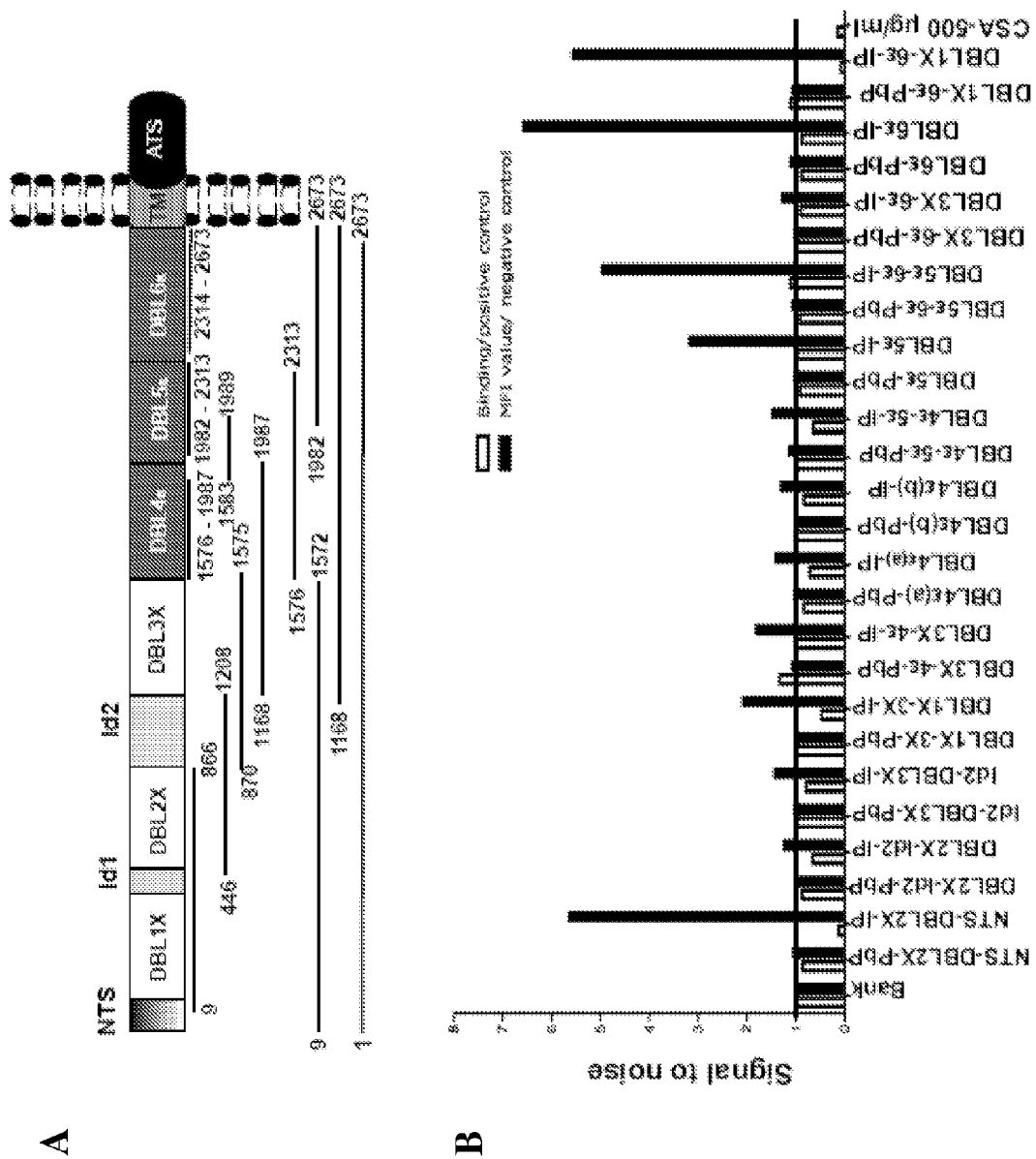
FIG. 1 shows the surface reactivity and anti-adhesion capacity of mice antisera to various VAR2CSA constructs. (A) is a schematic representation of the 13 overlapping VAR2CSA constructs made in a pVAX1 derivative vector. (B) Blood samples before immunization and from full bleeds at D75 were pooled for each group of 5 mice to constitute the pre-bleed pool (PbP) and immune pool (IP), respectively. The flow reactivity shown (black filled histograms) for each pool is defined as the Median Fluorescence Intensity (MFI) ratio (MFI test/MFI negative control). The negative controls were stained only with secondary FITC-conjugated anti-mouse antibody. Binding inhibition of infected erythrocytes to decorin (bovine CSPG) was measured using serum in a 1:5 dilution (white filled histograms). The degree of inhibition was defined as [1−(bound infected erythrocytes with test serum/bound infected erythrocytes without serum)].

The present invention generally relates to the use of specific regions of the extracellular domain of the VAR2CSA protein of the FCR3 parasite line for prevention and/or treatment of pregnancy-associated malaria.

I—NTS-DBL1x-Id1-DBL2x and Biologically Active Fragments Thereof NTS-DBL1x-Id1-DBL2x-Derived Polypeptides and Polynucleotides The present invention relates to polynucleotides and polypeptides derived from the extracellular domain of VAR2CSA and involved in pregnancy-associated malaria, and to their use in the treatment and/or prevention of pregnancy-associated malaria. The var2csa gene has been isolated and sequenced for several parasite strains, including FCR3 (GenBank Accession Number: AY372123). The sequence of the corresponding VAR2CSA has been deduced (GenBank Accession Number: AAQ73926.1).

More specifically, the present invention provides isolated polypeptides that consist of the NTS-DBL1x-Id1-DBL2x region of the VAR2CSA protein, or a biologically fragment thereof that comprises at least the Id1-DBL2x region of the VAR2CSA protein.

The term "isolated", as used herein in reference to a polypeptide or polynucleotide, means a polypeptide or polynucleotide, which by virtue of its origin or manipulation is separated from at least some of the components with which it is naturally associated or with which it is associated when initially obtained. By "isolated", it is alternatively or additionally meant that the polypeptide or polynucleotide of interest is produced, synthesized and/or purified by the hand of man.

The terms "protein", "polypeptide" and "polypeptide sequence" are used herein interchangeably. They refer to a sequence of amino acids (either in their neutral (uncharged) forms or as salts, and either unmodified or modified by glycosylation, side chain oxidation, or phosphorylation) that are linked through peptide bonds. In certain embodiments, the amino acid sequence is a full-length native protein. In other embodiments, the amino acid sequence is a smaller portion of the full-length protein. In still other embodiments, the amino acid sequence is modified by additional substituents attached to the amino acid side chains, such as glycosyl units, lipids, or inorganic ions such as phosphates, as well as modifications relating to chemical conversions of the chains such as oxidation of sulfydryl groups. Thus, the term "protein" (or its equivalent terms) is intended to include the amino acid sequence of the full-length native protein, or a portion thereof, subject to those modifications that do not significantly change its specific properties. In particular, the term "protein" encompasses protein isoforms, i.e., variants that are encoded by the same gene, but that differ in their pI or MW, or both. Such isoforms can differ in their amino acid sequence (e.g., as a result of allelic variation, alternative splicing or limited proteolysis), or in the alternative, may arise from differential post-translational modification (e.g., glycosylation, acylation, phosphorylation).

The terms "fragment", "portion" and "region" are used herein interchangeably. When used herein in reference to a protein, they refer to a polypeptide having an amino acid sequence of at least 5 consecutive amino acid residues (preferably, at least about: 10, 15, 20, 25, 30, 35, 40, 50, 60, 70, 80, 90, 100, 125, 150, 175, 200, 250 or more consecutive amino acid residues) of the amino acid sequence of the protein. The fragment of a protein may or may not possess a functional activity of the protein.

The term "biologically active", as used herein to characterize a protein variant, analogue or fragment, refers to a molecule that shares sufficient amino acid sequence identity or homology with the protein to exhibit similar or identical properties to the protein. For example, a biologically active fragment of NTS-DBL1x-Id1-DBL2x is a fragment that retains the ability of the NTS-DBL1x-Id1-DBL2x region of VAR2CSA to induce the production of antibodies that prevent adherence of *Plasmodium falciparum*-infected erythrocytes to the placenta receptor CSA.

The terms "NTS-DBL1x-Id1-DBL2x", "NTS-DBL1x-DBL2x" and "NTS-DBL2x" are used herein interchangeably. They refer to a N-terminal sequence (NTS) of VAR2CSA consisting of the following subdomains: Duffy-binding-like domain 1x (DBL1x), interdomain 1 (Id1) and Duffy-binding-like domain 2x (DBL2x) of VAR2CSA. In certain embodiments, NTS-DBL1x-Id1-DBL2x has the sequence corresponding amino acids 8 to 866 of VAR2CSA, i.e., has the sequence set forth in SEQ ID NO: 1, or a homologous sequence thereof.

The term "Id1-DBL2x" refers to a polypeptide consisting of the following subdomains: the interdomain 1 (Id1) and Duffy-binding-like domain 2x (DBL2x) of VAR2CSA. In certain embodiments, Id1-DBL2x has the sequence corresponding amino acids 392 to 866 of VAR2CSA, i.e., has the sequence set forth in SEQ ID NO: 2, or a homologous sequence thereof.

The term "homologous" (or "homology"), as used herein, is synonymous with the term "identity" and refers to the sequence similarity between two polypeptide molecules. When a position in both compared sequences is occupied by the same amino acid residue, the respective molecules are then homologous at that position. The percentage of homology between two sequences corresponds to the number of matching or homologous positions shared by the two sequences divided by the number of positions compared and multiplied by 100. Generally, a comparison is made when two sequences are aligned to give maximum homology. The optimal alignment of sequences may be performed manually or using softwares (such as GAP, BESTFIT, BLASTP, BLASTN, FASTA, and TFASTA, which are available on the NCBI site or in Wisconsin Genetics Software Package, Genetics Computer Group, Madison, Wis.). Homologous amino acid sequences share identical or similar amino acid sequences. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g. that have a similar size, shape, electric charge, chemical properties, including the ability to form covalent or hydrogen bonds, or the like. Particularly preferred conservative substitutions are those fulfilling the criteria defined for an "accepted point mutation" as described by Dayhoff et al. ("Atlas of Protein Sequence and Structure", 1978, Nat. Biomed. Res. Foundation, Washington, D.C., Suppl. 3, 22: 354-352).

The present invention also provides fusion proteins consisting of at least one polypeptide described herein fused to at least fusion partner.

The terms "fusion partner" and "fusion partner sequence" are used herein interchangeably, and refer to an amino acid sequence that confers to the fusion protein one or more desirable properties. Thus, a fusion partner may be a protein that improves the expression of the NTS-DBL1x-Id1-DBL2x region, or biologically active fragment thereof, in host cells during preparation of the fusion protein, and/or a protein that facilitates purification of the fusion protein, and/or a protein that increases the stability (e.g., plasma stability) of the fusion protein (compared to the stability of the non-fused protein), and/or a protein that improves or facilitates administration of the fusion protein to the subject being treated, and/or a protein that increases the desired therapeutic effect (for example by increasing the immune and vaccinal response), and/or a protein exhibiting a desirable biological or therapeutic activity.

Fusion partners that can be used in the context of the invention include, but are not limited to, maltose binding protein, signal sequence of the maltose binding protein, poly-histidine segments capable of binding metallic ions, S-Tag, glutathione-S-transferase, thioredoxin, β-galactosidase, streptavidin, dihydrofolate reductase, pelB signal sequence, ompA signal sequence, signal sequence of alkaline phosphatase, green fluorescent protein (GFP), toxins such as, for example, E. Coli enterotoxin LT or B-subunit thereof, a domain of tetanus toxin fragment C, cholera toxin or B-subunit thereof, CTA1-DD. Other fusion partners may be human growth hormone, an immunostimulating cytokine such as: interleukin-2 (IL-2), a growth factor such as granulocyte macrophage colony stimulating factor (GM-CSF), granulocyte colony stimulating factor (G-CSF), peptides or hormones such as: calcitonin, interferon-beta, interferon-alpha, glucagon like peptide 1 (GLP-1), glucagon like peptide 2 (GLP-2), PA toxin, parathyroid hormone (PTH(1-34) and PTH(1-84)), butyrylcholinesterase, glucocerebrosidase (GBA), and exendin-4.

The present invention also provides isolated polynucleotides for use in the treatment or prevention of pregnancy-associated malaria, the polynucleotides consisting of a sequence encoding a polypeptide or a fusion protein according to the invention and elements necessary to the in vitro or in vivo expression of said polypeptide or fusion protein. Preferably, the elements necessary to the in vitro or in vivo expression of the polypeptide or fusion protein are operably linked to the polynucleotide sequence to be transcribed.

The terms "nucleic acid sequence", "nucleic acid", "nucleic acid molecule", "polynucleotide" and "oligonucleotide" are used herein interchangeably. They refer to a given sequence of nucleotides, modified or not, which defines a region of a nucleic acid molecule and which may be either under the form a single strain or double strain DNAs or under the form of transcription products thereof.

The terms "elements necessary to the in vitro or in vivo expression of the polypeptide" and "elements necessary to the in vitro or in vivo transcription of the polynucleotide" are used herein interchangeably. They refer to sequences known in the art that allow the expression, and optionally the regulation, of a polypeptide (or the transcription of the polynucleotide sequence encoding the polypeptide) in a host cell or in vivo. Such elements include at least a transcription initiation sequence (also called promoter) and a transcription termination sequence that are function in a host cell or in vivo. The term "operably linked" refers to a functional link between the regulatory sequences and the nucleic acid sequence that they control.

Preparation of NTS-DBL1x-Id1-DBL2x-Derived Polypeptides and Polynucleotides

The polynucleotides and polypeptides of the present invention may be prepared using any suitable method known in the art.

Techniques to isolate or clone a gene or a nucleotide sequence encoding a specific domain of a protein are known in the art and include, for example, isolation from genomic DNA, preparation from cDNA, or combination of these methods. Cloning a gene, or an acid nucleic sequence encoding a specific domain of a protein, from genomic DNA may be performed for example using a polymerase chain reaction (PCR) or by screening expression libraries to detect cloned DNA fragments with identical structural characteristics (Innis et al., "PCR: A Guide to Method and Application", 1990, Academic Press: New York). Other amplification methods of nucleic acid molecules known in the art may be used, such as for example, ligase chain reaction (LCR), ligation activated transcription (LAT) and Nucleic Acid Sequence Based Amplification (NASBA). It is also possible to use a chemical method of synthesis to prepare a polynucleotide sequence. Chemical methods of synthesis of DNA or RNA strains are known to those skilled in the art, and involve the use of commercially available automatic synthesizers.

Methods to prepare polypeptides sequences include chemical methods (R. B. Merrifield, J. Am. Chem. Soc. 1963, 85: 2149-2154; "*Solid Phase Peptide Synthesis*", Methods in Enzymology, G. B. Fields (Ed.), 1997, Academic Press: San Diego, Calif.) and recombinant methods (Sambrook et al., *Molecular Cloning: A Laboratory Manual*, $2^{nd}$ Ed., 1989, Cold Spring Harbor Press: Cold Spring, N.Y.) using host cells.

A recombinant method for the production of NTS-DBL1x-Id1-DBL2x is described in the Examples provided below.

Cloning or Expression Vectors

The present invention also relates to cloning or expression vectors that allow expression of NTS-DBL1x-Id1-DBL2x, or biologically active fragments thereof, in host cells. More specifically, the present invention provides cloning or expression vectors comprising at least one polynucleotide or one fusion protein described herein. The cloning or expression vectors may be phages, plasmids, cosmids or viruses.

Host cells transformed or transfected with a polynucleotide or cloning or expression vector described herein are also encompassed in the present invention. Such host cells may be bacteria, yeast, insect cells or mammal cells.

II—Immunogenic Compositions and Vaccines

Polypeptides and polynucleotides of the invention are particularly suitable for use as drugs in the management of malaria in pregnant women. Indeed as demonstrated in the Examples section, the polypeptides of the invention are antigenic regions of the VAR2CSA protein involved in the acquisition of protective immunity against the placental sequestration that takes place during pregnancy-associated malaria; and the polynucleotides of the invention encode these antigenic regions. They may be used as such, or under a modified form, as an immunogenic composition or a vaccine.

A suitable modification of polypeptides according to the invention is conjugation. Conjugates according to the invention comprise at least one polypeptide of the invention liked to a carrier. Conjugates may be obtained by coupling the polypeptide peptide to a physiologically acceptable, non-toxic, natural or synthetic carrier via a covalent bound. The carrier may be selected to increase the immunogenic properties of the polypeptide.

Methods for the preparation of such conjugates are known in the art. For example, international application number WO 2006/124712 describes methods of preparation of conjugates comprising a plurality of antigenic peptides of *Plasmodium falciparum* linked to a protein carrier that improves the antigens immunogenicity.

Preferred carriers according to the invention include, but are not limited to, viral particles, lipids such as for example C16-C18 lipids, polylysines, poly(DL-alanine)-poly(Lysine)s, nitrocellulose, polystyrene microparticles, latex beads, biodegradable polymers, polyphosphoglycane microparticles, protein carriers such as OPMC (outer membrane protein complex of Neisseria meningitidis) or improved OPMC, BSA (bovine serum albumin), TT (tetanus toxoid), ovalbumin, KLH (heyhole limpet hemocyanin), THY (bovine thyroglobulin), HbSAg and HBcAg of hepatitis B virus, rotavirus capside protein, protein L1 of human papilloma virus, VLP (virus like particle) of types 6, 11 and 16, tuberculin PPD (purified protein derivative).

The polypeptides, fusion proteins, conjugates, polynucleotides and vectors of the invention may advantageously be used as therapeutic agents, in particular formulated as immunogenic compositions or vaccines.

Immunogenic Compositions

An immunogenic composition according to the invention generally comprises at least one pharmaceutically acceptable carrier or excipient and at least one member of the group consisting of polypeptides described herein, fusion proteins described herein, conjugates described herein, polynucleotides described herein, cloning or expression vectors described herein, and any combination thereof. The term "pharmaceutically acceptable carrier or excipient" refers to a carrier medium which does not interfere with the effectiveness of the biological activity of the active ingredient(s) and which is not excessively toxic to the individual at the concentration at which it is administered. The term includes solvents, dispersion, media, coatings, antibacterial and antifungal agents, isotonic agents, and adsorption delaying agents, and the like. The use of such media and agents for pharmaceutically active substances is well known in the art (see for example "*Remington's Pharmaceutical Sciences*", E. W. Martin, 18$^{th}$ Ed., 1990, Mack Publishing Co.: Easton, Pa., which is incorporated herein by reference in its entirety).

The formulation of an immunogenic composition according to the present invention may vary depending on the dosage and administration route selected. After formulation with at least one pharmaceutically acceptable carrier or excipient, an immunogenic composition according to the invention may be administered under any form suitable for human administration, for example solid or liquid form. One skilled in the art knows how to select carriers and/or excipients suitable to a given formulation.

Injectable preparations, for example sterile injectable aqueous or oleaginous suspensions, may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacteria-retaining filter, or by incorporating sterilizing agents in the form of sterile solid compositions which can be dissolved or dispersed in sterile water or other sterile injectable medium prior to use. Liquid pharmaceutical compositions that are sterile solutions or suspensions can be administered for example, by intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient, it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly(anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the active principles, the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizers or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and arachis oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, active ingredients may be mixed with at least one inert, physiologically acceptable excipient or carrier such as sodium citrate or dicalcium phosphate and one or more of: (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

In addition, in certain instances, it is expected that the inventive compositions may be disposed within transdermal devices placed upon, in, or under the skin. Such devices include patches, implants, and injections which release the active ingredient by either passive or active release mechanisms. Transdermal administrations include all administrations across the surface of the body and the inner linings of bodily passage including epithelial and mucosal tissues. Such administrations may be carried out using the present compositions in lotions, creams, foams, patches, suspensions, and solutions.

Transdermal administration may be accomplished through the use of a transdermal patch containing active ingredients and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

In certain preferred embodiments, the immunogenic compositions and vaccines of the invention may comprise one or more adjuvants used in combination. Examples of suitable classical adjuvants include Montanide et/ou l'Alum. Other suitable adjuvants include, but are not limited to, incomplete Freund's adjuvant, QS21, SBQS2, MF59, mLT, PHL, CpG DNA, calcium phosphate, dehydrated calcium sulfate, PLG, CT, LTB, CT/LT, AS02A, aluminium phosphate, aluminium hydroxide, monophosphoryl lipid A (MPL), a saponin, vitamin A, and various water-in-oil emulsions prepared from biodegradable oils such as squalene and/or tocopherol, Quil A, Ribi Detox, CRL-1005, L-121 and combinations thereof.

Immunogenic compositions and vaccines according to the invention may further comprise at least one antigen specific of preerythrocytic stages (CSP, TRAP, LSA-1, LSA-3, SALSA, STARP, EXP-1), asexual erythrocytic stages (MSP-1, MSP-3, AMA-1, EBA-175, GLURP, MSP-2, MSP-4, MSP-5, RAP-2, RESA, PfEMP-1, synthetic GPI toxin) or sexual erythrocytic sages (PfS25).

Vaccines, Protein Vaccines, DNA Vaccines

A vaccine against pregnancy-associated malaria according to the present invention generally comprises at least polypeptide described herein, at least one polynucleotide described herein, or at least one cloning or expression vector described herein, and is used to induce, in treated subjects, antibodies capable of inhibiting the binding of infected erythrocytes to CSA. In particular, the invention provides a DNA vaccine (also called plasmid vaccine or polynucleotide vaccine) against placental malaria. The invention also provides a protein vaccine (also called polypeptide vaccine) against placental malaria.

Protein Vaccines

More specifically, the invention provides a protein vaccine comprising a polypeptide consisting of the NTS-DBL1x-Id1-DBL2x region of the VAR2CSA protein, or a biologically active fragment thereof comprising at least the Id1-DBL2x region of the VAR2CSA protein. In certain preferred embodiments, the NTS-DBL1x-Id1-DBL2x region has the sequence set forth in SEQ ID NO: 1, or a homologous sequence thereof. In certain preferred embodiments, the Id1-DBL2x region has the sequence set forth in SEQ ID NO: 2, or a homologous sequence thereof. In certain embodiments, the polypeptide is fused to at least one fusion partner, as described herein.

The administration of a protein vaccine according to the present invention may be performed using any suitable route, such as for example, intravenously, sub-cutaneously, intradermically, orally, topically or systemically.

DNA Vaccines

The present invention also relates to a DNA vaccine against pregnancy-associated malaria. Genetic vaccination or DNA vaccination is aimed at inducing an immune response and consists in the direct introduction, in certain cells, of a gene or a nucleotide sequence encoding a vaccinal antigen or of a purified DNA plasmid comprising a sequence encoding a vaccinal antigen. In the Examples presented herein, DNA vaccination was performed on muscle cells. However, DNA vaccination may be performed on other types of cells, such as for example, cells of the skin. Examples of methods of administration of a DNA vaccine include, but are not limited to, intra-muscular injection, particle "bombardment" to the skin, and nasal administration. The DNA penetrates in the targeted muscle cells, skin cells or other types of cells; and these cells then synthesize the antigen. The synthesized antigen is presented to the immune system, and initiates a response (the production of antibodies that have the ability, in case of infection, to specifically recognize that particular antigen on the parasite). The vaccine is thus produced locally by the organism of the immunized individual. This method of vaccination is simple and inexpensive, and presents important advantages in terms of efficiency. Indeed, the antigen thus produced is generally under the form of the native peptide sequence, fused or not to one or more peptidic sequences (fusion partners). Furthermore, it is produced in a temporally extended fashion by cells of the organism, and this lengthy production and presentation of the antigen should prevent the need of booster vaccines. In addition, DNA vaccines are chemically defined and thermally stable, which reduces the need to maintain an unbroken cold chain.

Therefore, the present invention provides a DNA vaccine comprising a naked DNA, in particular a circular vaccinal plasmid (either super-coiled or not) or a linear DNA molecule, comprising and expressing in vivo a nucleotide sequence encoding a polypeptide consisting of the NTS-DBL1x-Id1-DBL2x region of the VAR2CSA protein, or a biologically active fragment thereof comprising at least the Id1-DBL2x region of VAR2CSA. The term "naked DNA", as used herein, has its art understood meaning and refers to a DNA transcription unit under the form of a polynucleotide sequence comprising at least one nucleotide sequence encoding a vaccine antigen and elements necessary to the expression of the nucleotide sequence in vivo. Polynucleotides according to the invention may advantageously be inserted into a plasmid such as DNA-CSP, Nyvac pf7, VR1020, VR1012, etc.

The elements necessary to the expression of a nucleotide sequence in vivo include, but are not limited to, a promoter or transcription initiation region, and a transcription termination region that are functional in a human cell. In addition, sequences that increase the genetic expression, such as introns, "enhancer" sequences and "leader" sequences are often necessary for the expression of a sequence encoding an immunogenic protein. As known in the art, these elements are preferably operably linked to the nucleotide sequence that is to be transcribed.

Examples of promoters useful in DNA vaccines, in particular, in DNA vaccines intended to be used in human vaccination, include, but are not limited to, SV40 virus promoter, mouse mammary tumor virus-like virus (MMTV) promoter, HIV virus promoter, Moloney virus promoter, cytomegalovirus (CMV) promoter, Epstein-Barr virus (EBV) promoter, Rous sarcoma virus (RSV), as well as promoters of human genes such as actin gene promoter, myosin gene promoter, hemoglobulin gene promoter, muscle creatin gene promoter, and metallothionein gene promoter.

One skilled in the art knows how to construct a DNA vaccine.

The naked DNA may also be incorporated into a drug carrier. Examples of suitable drug carriers include, but are not limited to, biodegradable microcapsules, immunostimulating complexes, liposomes, cationic lipids, and live, attenuated vaccine vectors such as viruses and bacteria.

A DNA vaccine according to the invention may also be administered in combination with an agent that improves or favors the penetration of a vaccine genetic material into cells. Thus, a DNA vaccine may be formulated to contain such an agent or be administered at substantially the same time as such an agent. Examples of agents that improve the penetration of a vaccine genetic material into cells include, but are not limited to, esters of benzoic acid, anilides, amidines, urethanes, and hydrochloride salts thereof (U.S. Pat. No. 6,248,565). The administration of DNA to cells may be improved using chemical vectors (such as, for example, cationic polymers or cationic lipids), physical technical such as electroporation, sonoporation, magnetofection, etc, or using viral vectors such as adenoviruses, etc.

III—Uses of Immunogenic Compositions and Vaccines

The immunogenic compositions and vaccines according to the present invention may be used to immunize female human beings (and more specifically prepubertal girls and women in age of bearing children, in particular postpubertal girls or primigravidae) with the goal of preventing pregnancy-associated malaria.

Consequently, the invention relates to methods of treatment or prevention of pregnancy-associated malaria. More specifically, the invention provide a method for inducing a protective immune response against *Plasmodium falciparum* in a female human being, the method comprising a step of administering, to the female human being, an effective amount of an immunogenic composition or vaccine described herein. The invention also provides a method of vaccination of a female human being against pregnancy-related malaria, the method comprising a step of administering, to the female human being, an effective amount of a vaccine of the invention, in particular a DNA vaccine or a protein vaccine described herein.

As used herein, the term "effective amount" refers to any amount of an immunogenic composition or vaccine that is sufficient to fulfil its intended purpose(s). For example, in certain embodiments of the present invention, the purpose(s) may be: to prevent pregnancy-associated malaria, and/or to induce the production of antibodies that inhibit binding of *P. falciparum*-infected erythrocytes to placental CSA, and/or to treat pregnancy-associated malaria.

In these methods, administration of an immunogenic composition or a vaccine may be performed using any suitable route (e.g., orally, parentally, mucosally). In certain embodiments, a DNA vaccine is administered intramuscularly, intradermically or mucosally. In other embodiments, a protein vaccine is administered intraveinously, sub-cutaneously, intradermally, orally, topically or systemically.

An immunogenic composition or a vaccine according to the invention may be administered in a single dose or in several doses. The attending physician will know, or will know how to determine, the efficient dose and appropriate administration regimen to be used in a given protocol of immunization or vaccination.

IV—Kits

The present invention also provides pharmaceutical packs or kits for the prevention of pregnancy-associated malaria. More specifically, a pharmaceutical pack or kit comprises materials that are necessary to perform a vaccination according to the invention. Generally, a kit comprises an immunogenic composition or vaccine according to the invention, and instructions to perform the vaccination. Optionally, the kit can further comprise means to perform a vaccination.

The kit will comprise one or more containers (e.g., vials, ampoules, test tubes, flasks or bottles) containing one or more ingredients of an inventive immunogenic composition or vaccine, allowing administration according to the invention. Different ingredients of a pharmaceutical pack or kit may be supplied in a solid (e.g., lyophilized) or liquid form. Each ingredient will generally be suitable as aliquoted in its respective container or provided in a concentrated form. Pharmaceutical packs or kits may include media for the reconstitution of lyophilized ingredients. Individual containers of the kits will preferably be maintained in close confinement for commercial sale.

Optionally associated with the container(s) can be a notice or package insert in the form prescribed by a governmental agency regulating the manufacture, use or sale of pharmaceutical or biological products, which notice reflects approval by the agency of manufacture, use or sale for human administration. The notice of package insert may contain instructions for use of an immunogenic composition or vaccine according to methods of vaccination or treatment disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

Unless specified otherwise, all the technical and scientific terms used herein have the same meaning as that generally understood by a regular expert in the field of this invention. Similarly, any publications, patent applications, patents and any other references mentioned herein are included by reference.

The following examples and the figures are described to illustrate some embodiments of the procedures described above and should in no way be considered to be a limitation of the scope of the invention.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained. Some of the results presented below have been described in a scientific paper (Bigey et al., "The NTS-DBL2x region of VAR2CSA induces cross-reactive antibodies that inhibit adhesion of *Plasmodium* isolates to Chondroitin-Sulfate A", J. Infect. Dis., 2011, in press), which is incorporated herein by reference in its entirety.

The studies presented below were approved by the Comité Consultatif de Déontologie et d'Ethique of the Research Institute for Development (France), the ethical committee of the Ministry of Health (Senegal), and the ethics committee of Health Science Faculty (University of Abomey-Calavi, Benin). All procedures, including the animal immunization procedures, complied with European and National regulations.

Example 1

Identification, Production and Analysis of NTS-DBL1x-Id1-DBL2x

In the study presented in this section, the possibility of identifying functionally important VAR2CSA regions that can induce IgGs with high adhesion inhibitory capacity has been investigating. Using intramuscular plasmid DNA electrotransfer, antibodies induced against a specific region of VAR2CA, the NTS-DBL1x-Id1-DBL2x, were shown to efficiently block parasite binding to CSA at a similar level as antibodies induced against the full-length extracellular domain of VAR2CA. The present work highlights an important achievement towards development of a protective vaccine against placental malaria.

Materials and Methods

Parasites and Human Plasma.

In vitro-propagated *P. falciparum* parasites FCR3, and HB3 grown in O+ erythrocytes without human serum, as previously described (Cranmer et al., Trans. R. Soc. Trop. Med. Hyg., 1997, 91: 363-365), were used in this study. Antibody reactivity with infected erythrocytes was tested on unselected cultures and cultures selected for infected erythrocytes adhesion to CSA. Cultures were selected following several panning on choriocarcinoma cell line BeWo, as described (Haase et al., Infect. Immun., 2006, 74: 3035-3038).

Primary field *P. falciparum* isolates and plasma samples were collected from a cohort of pregnant women enrolled in the ongoing STOPPAM project in the district of Comé, located 70 km West from the economical capital of Benin, Cotonou (Huynth et al., Malar. J., 2011, 31; 10(1): 72). The isolates were obtained either from the peripheral blood of children below the age of 5 years (N=5) and from pregnant women (N=24), or from placental blood at delivery (N=6). Peripheral blood isolates were maintained in vitro for no more than 48 hours before testing.

Plasma samples from a previous study conducted in Senegal were also used (Tuikue Ndam et al., J. Infect. Dis., 2004, 190: 2001-2009).

Animal Immunization and Antibody Screening.

The var2csa gene from the FCR3 parasite genome and a corresponding synthetic gene with a codon-optimized sequence (GenBank accession no. GU249598) as described in Khunrae et al. (Khunrae et al., J. Mol. Biol., 2010, 397: 826-8340 were used as cloning templates. Using constructs comprise of single and multiple domains of VAR2CA proteins, sequences were cloned into a pVax1 vector backbone (Invitrogen) in which the original cytomegalovirus (CMV) promoter was replaced with the CMV promoter of the pCMVb plasmid (Clontech), and fused to the mEPO signal sequence, as already described (Trollet et al., Infect. Immun., 2009, 77: 2221-2229).

In vitro immunizations were carried out on 6-week old Swiss female mice (Janvier, France) and on 2-month old New-Zealand rabbits (Grimaud, France). Electrotransfer experiments were carried out on mice, as previously described (Avril et al., PLoS One, 2011, 7:6(2): e16622). Briefly, mice were anesthetized by intraperitoneal injection of 0.3 mL of a mix of ketamine (100 mg/mL) and xylazine (10 mg/mL) in 150 mM NaCl. Hind legs were shaved. Plasmid DNA (40 µg) in saline was injected into the tibial cranial muscle. After injection, transcutaneous electric pulses (8 pulses of 200 V/cm and 20 ms duration at a frequency of 2 Hz) were applied by two stainless steel external plate electrodes placed abut 5 mm apart, at each side of the leg (Trollet et al., Infect. Immun., 2009, 77: 2221-2229).

For rabbit immunization, animals were anesthetized by intramuscular injection of a mix of ketamine (35 mg/kg) and xylazine (5 mg/kg). The backs of the rabbits were shaved, and 300 µg of plasmid DNA in plasmid were injected in 5 different sites of each longissimus dorsi muscle with a 3-needle electrode device. After injection, electrical pulses (8 pulses of 120 V/cm and 20 ms duration at a frequency of 2 Hz) were applied at each injection site by means of a 3-needle electrode device.

All animals (mice and rabbits) were immunized three times: at days 0, 30 and 60, and antisera were collected 15 days after the second and the last immunization (i.e., at days 45 and 75).

For protein immunization, mouse antisera were also produced by the intraperitoneal injection of 1014 of the recombinant protein in 50 mL, mixed with an equal volume of Alugel. Mice were immunized three times: at days 0, 30 and 60. Antisera were collected 15 days after the final boosting injection (i.e., at day 75).

IgG Preparation.

Total IgG was manually purified from final bleed mice/rabbit sera on a HI-TRAP® Protein G HP column according to the manufacturer's recommendations (GE Healthcare). Construct-specific IgGs were affinity purified from plasma pools of women exposed to pregnancy-associated malaria and from exposed male using HI-TRAP® NHS-activated HP columns (GE Healthcare) on which the corresponding recombinant protein was coupled following the manufacturer's recommendations.

Antibody Reactivity with *P. falciparum* Laboratory Lines and Field Isolates.

In vitro-propagated *P. falciparum* parasites FCR3 and HB3 were repeatedly panned on the human choriocarcinoma cell line BeWo, as previously described (Haase et al., Infect. Immun., 2006, 74: 3035-3038). The derived CSA-adhering infected erythrocytes (FCR3-BeWo, HB3-Bewo) and 35 primary field *P. falciparum* isolates collected at Comé, southwestern Benin (Yadouleton et al., Malaria J., 2010, 9: 204) were analyzed to determine the reactivity of the antibodies generated.

Flow cytometry (FACS Calibur, Beckman Coulter) was used to test the reactivity of sera of vaccinated animals to the surface of infected erythrocytes, as previously described (Barfod et al., J. Immunol., 2010, 185: 7553-7561). In brief, CSA-selected parasite cultures or field parasite isolates were enriched to contain late trophozoite and shizont stage parasites by exposure to a strong magnetic field (VarioMACS and CS columns, Miltenyi). Aliquots ($2 \times 10^5$ infected erythrocytes) were labelled using ethidium bromide and sequentially exposed to mouse/human serum and anti-mouse/human IgG-FITC (Invitrogen). All samples relating to a particular parasite isolate were processed and analyzed in a single assay.

Protein Expression, Purification and Evaluation.

The NTS-DBL1x-Id1-DBL2x region of the var2csa gene from FCR3 parasite line (synthetic gene) was cloned into the baculovirus vector pAcGP67-A (BD Biosciences) upstream of a histidine tag in the C-terminal end of the construct. This construct was made to allow translation from amino acid N9 to amino acid A864. Linearized Bakpb6 Baculovirus DNA (BD Biosciences) was cotransfected with pAcGP67-A into Sf9 insect cells for production of recombinant virus particles. Hi5 insect cells grown in 600 mL serum-free media (Gibco, 10486) were infected with 18 mL of $2^{nd}$ amplification of the recombinant virus particles. After 2 days of induction, the cells were centrifuged (8.000 g, 4° C., 10 minutes) and the supernatant was filtered using two 10 kDa NMWC PES membranes (0.45 µm) (GE Healthcare). The supernatant was then concentrated to 30 mL and diafiltered six times on an ÄKTA crossflow (GE Healthcare) with buffer A (10 mM sodium phosphate, pH 7.4, 500 mM NaCl). The retentate was recovered from the system and filtered (0.2 μm). Before loading on the HIS-SELECT® column, imidazole (Sigma-Aldrich) (150 μL, 1 M, pH 7.4) was added to the sample, giving a final imidazole concentration of 15 μM. The bound protein was eluted with buffer A+200 mM imidazole (HIS-SELECT®). The eluted protein was subjected to gel filtration.

Specific recognition of the purified protein was evaluated in ELISA using plasma samples from pregnant women of Benin and Senegal, unexposed pregnant French women, and malaria-exposed children (from Senegal) and men (from Benin and from Senegal).

Inhibition of Infected Erythrocytes to CSPG by Specific IgG.

The static assays employed to evaluate the capacity of the antibodies to interfere with CSA-specific adhesion of infected erythrocytes was described in detail elsewhere (Fried et al., Methods Mol. Med., 2002, 72: 555-560). In this assay, plates were coated overnight at 4° C. with 20 μL of ligand: 1% BSA, 5 μg/mL decorin: CSPG (Chondroitin Sulfate Proteoglycan, Sigma) or 50 μg/mL bovine CSA (Sigma) diluted in PBS. Each spot was subsequently blocked with 3% BSA in PBS for 30 minutes at room temperature. Late-stage-infected erythrocytes were also blocked in BSA/RPMI for 30 minutes at room temperature. Parasite suspensions adjusted to 20% parasite density were incubated with serum (1:5 final dilution) or purified IgG (0.01 mg/mL to 1 mg/mL final concentration) or 500 μg/mL soluble CSA for 30 minutes at room temperature before they were allowed to bind to ligand for 15 minutes at room temperature. Non-adhering cells were removed by an automated washing system. Spots were fixed with 1.5% glutaraldehyde in PBS and adhering infected erythrocytes was quantified by microscopy.

Competition ELISA.

Prior to competition ELISA, the anti-NTS-DBL1x-Id1-DBL2x IgG titer was determined in plasma pools composed of samples from exposed multigravid women from Benin, DNA-vaccinated rabbits and protein-immunized mice (plasma pools from D75). Microtiter plates (Nunc) were coated with recombinant NTS-DBL1x-Id1-DBL2x (0.5 μg/mL in PBS). After the plates were saturated with blocking buffer (PBS, 0.5 M NaCl, 1% TRITON™ X-100, 1% BSA) for 1 hour at room temperature, they were incubated for 1 hour at room temperature with increasing dilutions of the competing plasma (plasma pools from D75 DNA-vaccinated rabbits or protein-vaccinated mice against NTS-DBL1x-Id1-DBL2x). Pre-immune sera pools of rabbit or mouse or plasma pool from unexposed French pregnant women were used as negative control. Plates were washed four times with washing buffer (PBS, 0.5 M NaCl, 1% TRITON™ X-100, pH 7.4) and incubated with a fixed dilution of one plasma/serum (Plasma pools from D75 DNA-vaccinated rabbits or sera from malaria-exposed Beninese multigravidae) for 1 hour at room temperature. The specific secondary antibody directed against the non-competing antibodies (goat anti-human IgG HRP, Sigma-Aldrich, goat anti-mouse IgG HRP or goat anti-rabbit IgG HRP, Sigma) diluted 1:4000 in blocking buffer was added, and incubated for 1 hour at room temperature. After a 4-times washing, antibody reactivity of nocompeting plasma/serum was visualized at 450 nm following the addition of TMB (tetramethylbenzidine). The percent reduction in antibody reactivity in the presence of a competitor was calculated as follows: 100×[OD competitor antibody/OD without competitor antibody].

Results

Plasmid DNA Immunization Induced High Titer Surface Reactive Antibodies.

A total of 13 plasmids representing single and overlapping multiple domains of VAR2CSA from the FCR3 parasite line were constructed and used for immunization (FIG. 1A). The single and overlapping domains of VAR2CSA that were tested are: NTS-DBL1x-Id1-DBL2x (corresponding to amino acids 8 to 866); DBL2x-Id2 (amino acids 446-1208); Id2-DBL3x (amino acids 870-1575); DBL3x-4ε (amino acids 1168-1987); DBL4ε(a) (amino acids 1576-1987); DBL4ε(b) (amino acids 1583-1989); DBL4ε-5ε (amino acids 1576-2313); DBL5ε (amino acids 1982-2313); DBL5ε-6ε (amino acids 1982-2673); DBL6ε (amino acids 2314-2673); NTS-DBL3x (amino acids 9-1572); DBL3x-DBL6ε (amino acids 1168-2673); and NTS-DBL6ε (amino acids 1-2673).

All immunizations with single to triple-domains constructs of VAR2CSA induced the formation of polyclonal antibodies with a high ELISA titer (>1×10$^5$) following intramuscular plasmid electrotranfer. However, for plasmids containing more than 3000 bp of coding sequence, effective humoral immune response in all vaccinated animals, both mice and rabbits, required the use of a codon-optimized sequence (GenBank Accession Number GU249598). Although all single and multi-domains of VAR2CSA could induce antibodies reacting with native VAR2CSA on the surface of the CSA adhering-erythrocytes infected with the homologous FCR3, constructs containing DBL1x, DBL2x, DBL5ε and DBL6ε were the most efficient in inducing surface reactive antibodies (FIG. 1B). None of the polyclonal anti-VAR2CSA antisera recognized the erythrocytes infected with the non-CSA adherent FCR3 parasite line.

Antibodies Induced Against VAR2CSA Inhibit Binding of Infected Erythrocytes to Chondroitin Sulfate Proteoglycan (CSPG).

Figure 2:
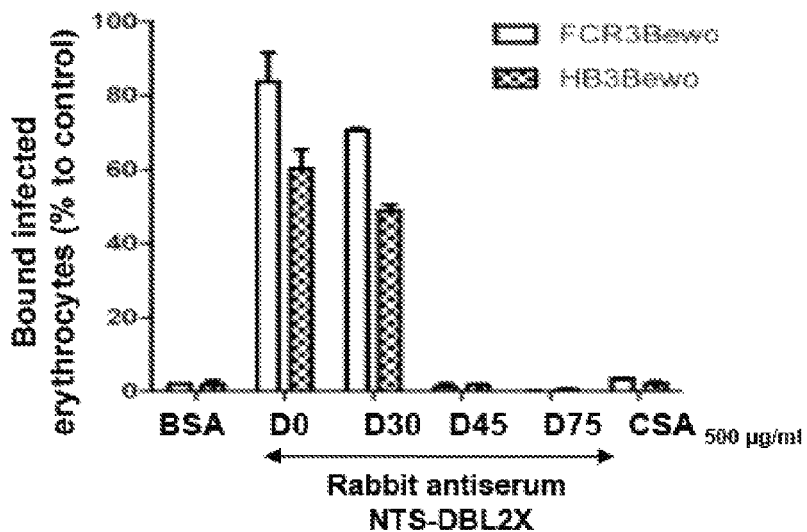
FIG. 2 shows that NTS-DBL1x-Id1-DBL2x induces adhesion-inhibitory IgGs in different animal species. (A) Two rabbits immunized with plasmids encoding the NTS-DBL1x-Id1-DBL2x of the FCR3 var2csa variant acquired anti-adhesion antibodies to both CFR3-BeWo and HB3-BeWo infected erythrocytes from the second immunization. (B) purified IgGs induced against the NTS-DBL1x-Id1-DBL2x region and purified IgGs induced against DBL6e recognize native VAR2CSA on the surface of FCR3-BeWo infected erythrocytes. However, they did not recognized unselected FCR3 infected erythrocytes (data not shown). IgGs purified from animals before vaccination did not label the surface of FCR3-BeWo infected erythrocytes. (C) Purified anti-NTS-DBL1x-Id1-DBL2x IgGs specifically inhibit binding of FCR3-BeWo infected erythrocytes to CDPG.
Figure 2:
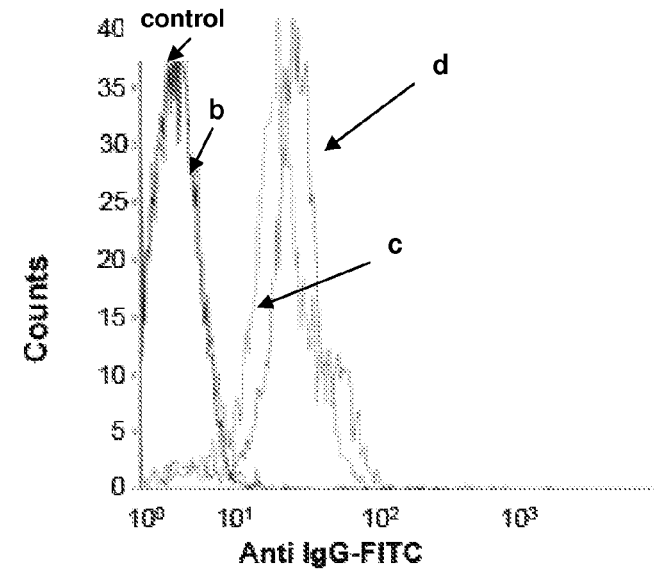
Figure 2:
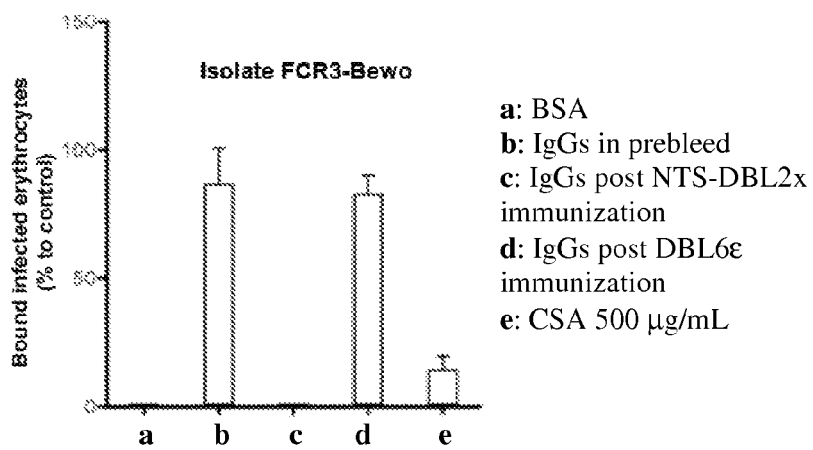
Figure 3:
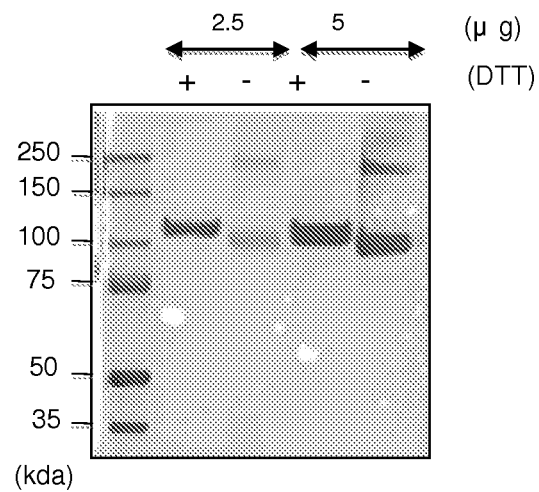
FIG. 3 is an SDS-PAGE of NTS-DBL1x-Id1-DBL2x of VAR2CSA purified on a 1 mL HisSelect ($Ni^{2+}$), 1 mL Capto S HP (IEX), and 1 mL of Heparin HP column (Hep), respectively. Samples of 2.5 and 5 µg of the purified recombinant protein were loaded for yield comparison.

A Petri dish-based static binding assay was used to screen sera for their ability to inhibit parasite binding to CSA. Of all the FCR3 VAR2CSA regions tested, only sequences located between the N-terminal sequence (NTS) and the DBL3x appeared to induce inhibitory antibodies (FIG. 1B). Highly inhibitory antibodies were obtained with the full-length extracellular VAR2CSA construct, which totally inhibited binding. Interestingly, similar inhibition was seen with sera from animals (both mice and rabbits) vaccinated with the NTS-DBL1x-Id1-DBL2x construct. In addition, the inhibitory activity of sera from NTS-DBL1x-Id1-DBL2x vaccinated animals was investigated on a heterologous parasite line; the CSA adherent HB3 line. The same pattern of inhibition was observed (FIG. 2A).

To confirm that the inhibition observed with NTS-DBL1x-Id1-DBL2x antiserum was mediated by IgG, IgGs were purified and tested for binding inhibition activity. The purified IgGs recognized the surface of BeWo-selected FCR3 infected erythrocytes (FIG. 2B). The purified IgGs inhibited 100% of the binding of infected erythrocytes to CSA at a concentration of 0.5 mg/mL (FIG. 2D).

Antibodies Induced Against NTS-DBL1x-Id1-DBL2x Specifically Recognized Isolates from Pregnant Women.

Flow cytometry analysis clearly demonstrated that murine anti-NTS-DBL1x-Id1-DBL2x antibodies specifically recognize the surface of placental malaria parasites among the field isolates. Thirty five (35) isolates were analyzed by flow cytometry in this study, including 24 peripheral blood isolated from pregnant women. Six placental isolates and 21 of the 24 peripheral blood isolates from pregnant women were recognized by polyclonal murine antibodies while none of the 5 children isolates tested were labelled.

Of the 21 isolates from pregnant women that reacted with anti-NTS-DBL1x-Id1-DBL2x antibodies by flow cytometry, 16 showed specific adhesion to CSPG, while 5 isolates did not bind. Among the 3 peripheral blood isolates that were not labelled in flow cytometry, 2 bound to CSPG but their interaction could not be abrogated by soluble CSA, and 1 isolate did not bind.

Fifteen samples containing sufficient amount of parasite were further processed in binding inhibition assay. These comprised 14 isolates from peripheral blood samples and one placental isolate. The binding to CSA of 12 of the 15 pregnant women isolates tested as highly inhibited by specific anti-NTS-DBL1x-Id1-DBL2x sera (see Table 1 below).

TABLE 1

Adhesion inhibitory capacity of specific antibodies induced against NTS-DBL2x on *P. falciparum*-infected erythrocytes from naturally infected pregnant women in Benin.

| Isolates | Bound IEs/ mm² on BSA | Bound IEs/ mm² on CSPG | MFI (ratio to negative control) | % prebleed inhibition | % anti- NTS- DBL2x inhibition | % CSA inhibition |
|---|---|---|---|---|---|---|
| CM0425 | 1 | 1035 | 3.2 | 0.00 | 41.75 | 92.21 |
| WP0182 | 2 | 339 | 3.8 | 23.92 | 74.75 | 94.16 |
| CM0375 | 5 | 63 | 1.6 | 0.00 | 51.32 | 94.23 |
| WP0140 | 2.5 | 244 | 1.8 | 16.36 | 61.65 | 98.98 |
| WP0161 | 1 | 1301 | 21.0 | 32.26 | 87.34 | 90.75 |
| WP0168 | 2 | 473 | 6.4 | 0.00 | 42.35 | 94.16 |
| CM0437 | 1 | 736 | 4.1 | 29.89 | 94.56 | 93.34 |
| WP0200 | 4.5 | 185 | 1.4 | 0.00 | 31.79 | 68.29 |
| CM445 | 1.5 | 218 | 2.2 | 28.69 | 76.27 | 87.62 |
| AK366 | 0.5 | 357 | 4.3 | 15.91 | 63.35 | 95.99 |
| AK357 | 2.5 | 337 | 1.5 | 20.66 | 58.04 | 91.12 |
| WP203 | 1 | 161 | 4.2 | 31.26 | 82.68 | 85.87 |
| 1MH016 | 2 | 178 | 2.0 | 16.48 | 53.92 | 85.04 |
| 1MMCH | 2.5 | 394 | 3.1 | 1.89 | 72.87 | 86.48 |
| CM307 | 1 | 623 | 5.9 | 17.83 | 89.45 | 96.30 |

Animals Immunized with Recombinant NTS-DBL1x-Id1-DBL2x or DNA Electrotransfer Produced Antibodies of Similar Specificity.

Figure 4:
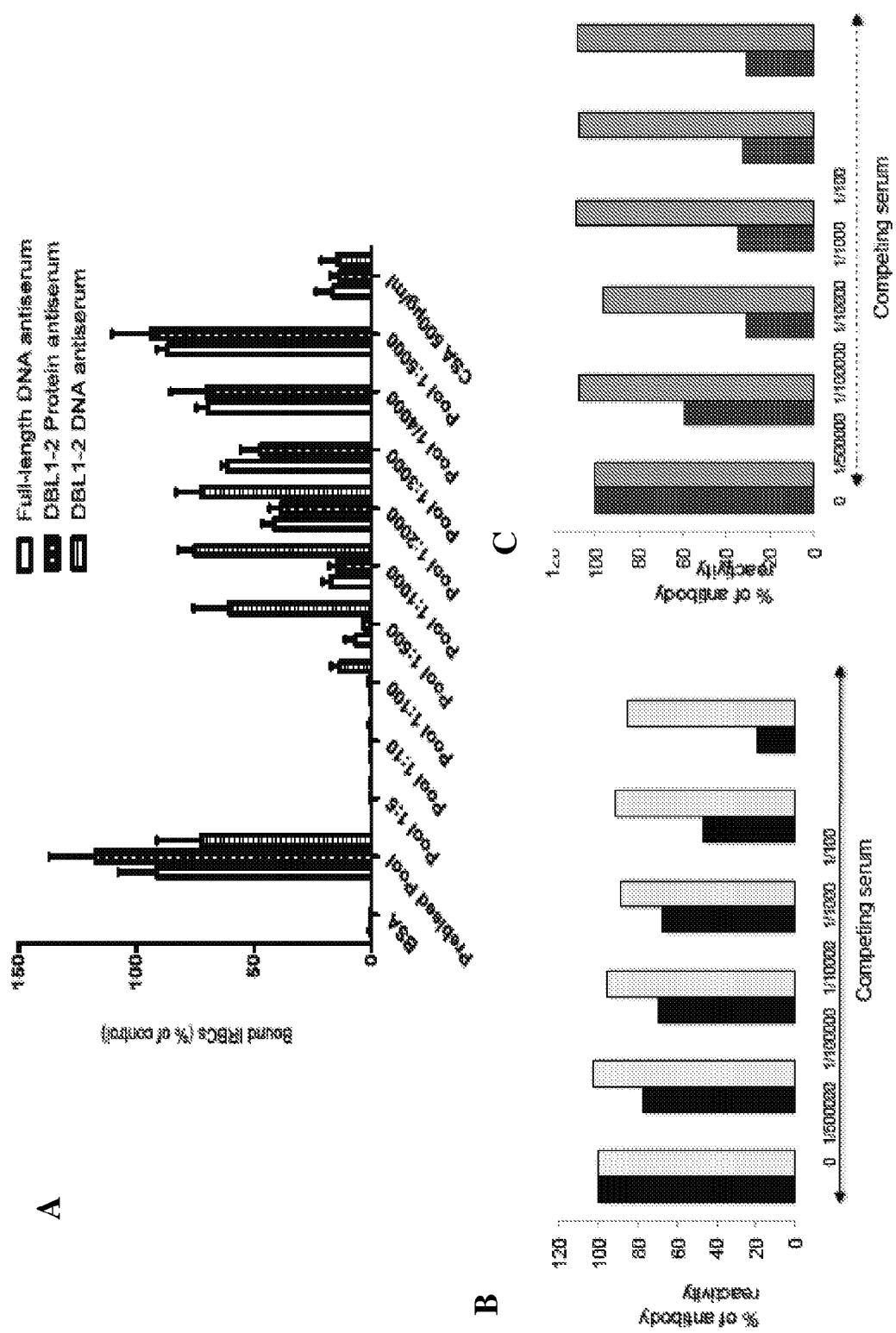
FIG. 4 shows that experimentally induced or naturally acquired antibodies against NTS-DBL1x-Id1-DBL2x target common epitopes. (A) Anti-adhesion capacity in a dilution series of hyperimmune mice antisera on the binding of FCR3-BeWo infected erythrocytes to CSPG. The proportion of infected erythrocytes binding to CSPG in the presence of the indicated dilutions of the D75 antiserum is shown compared to control binding without competition. Antisera induced by DNA immunization with the full length (empty histograms) or NTS-DBL2x (stripped histograms) or by the baculovirus-expressed recombinant NTS-DBL2x (dotted histograms) were used. BSA indicates the binding of infected erythrocytes to bovine serum albumin. (B) Competitive recognition of recombinant NTS-DBL1x-Id1-DBL2x between specific antibodies induced by genetic immunization versus protein immunization. Sera from protein-vaccinated mice and the corresponding pre-bleed are the competing antibodies. D75 serum from DNA vaccinated rabbit is used as non-competing antibodies. (C) Competitive recognition of recombinant NTS-DBL1x-Id1-DBL2x between antibodies produced by genetic immunization in rabbits and naturally acquired in the plasma of malaria-exposed pregnant women from Benin. The competing sera are: D75 serum from DNA vaccinated rabbit, and the corresponding rabbit pre-immune serum. The non-competing antibodies are represented by a pool of Beninese multigravidae plasma.

Murine polyclonal antibodies induced either by recombinant protein or plasmid DNA of NTS-DBL1x-Id1-DBL2x showed similar reactivity. The reactivity to erythrocytes surface and inhibitory activity on binding to CSA were similar on BeWo-selected FCR3 infected erythrocytes. The inhibitory activity was compared in dilution series of sera from mice immunized with either the full-length construct or NTS-DBL1x-Id1-DBL2x (both DNA and protein immunization). Down to the dilution 1:100, sera from mice vaccinated with full-length DNA construct or recombinant NTS-DBL1x-Id1-DBL2x totally inhibited binding of infected erythrocytes (FIG. 4A). The inhibitory capacity of the serum samples following plasmid DNA immunization with the full-length construct or by protein vaccination with NTS-DBL1x-Id1-DBL2x was seen at subsequent dilutions, these sera were diluted 1:5000 before inhibition vanished (FIG. 4A). This observation clearly strengthens the importance of the NTS-DBL1x-Id1-DBL2x region of VAR2CSA in eliciting adhesion-inhibitory antibodies by vaccination.

Antibodies Induced in Animals by Vaccination with NTS-DBL1x-Id1-DBL2x Target the Same Epitopes as Naturally Acquired Antibodies.

Figure 5:
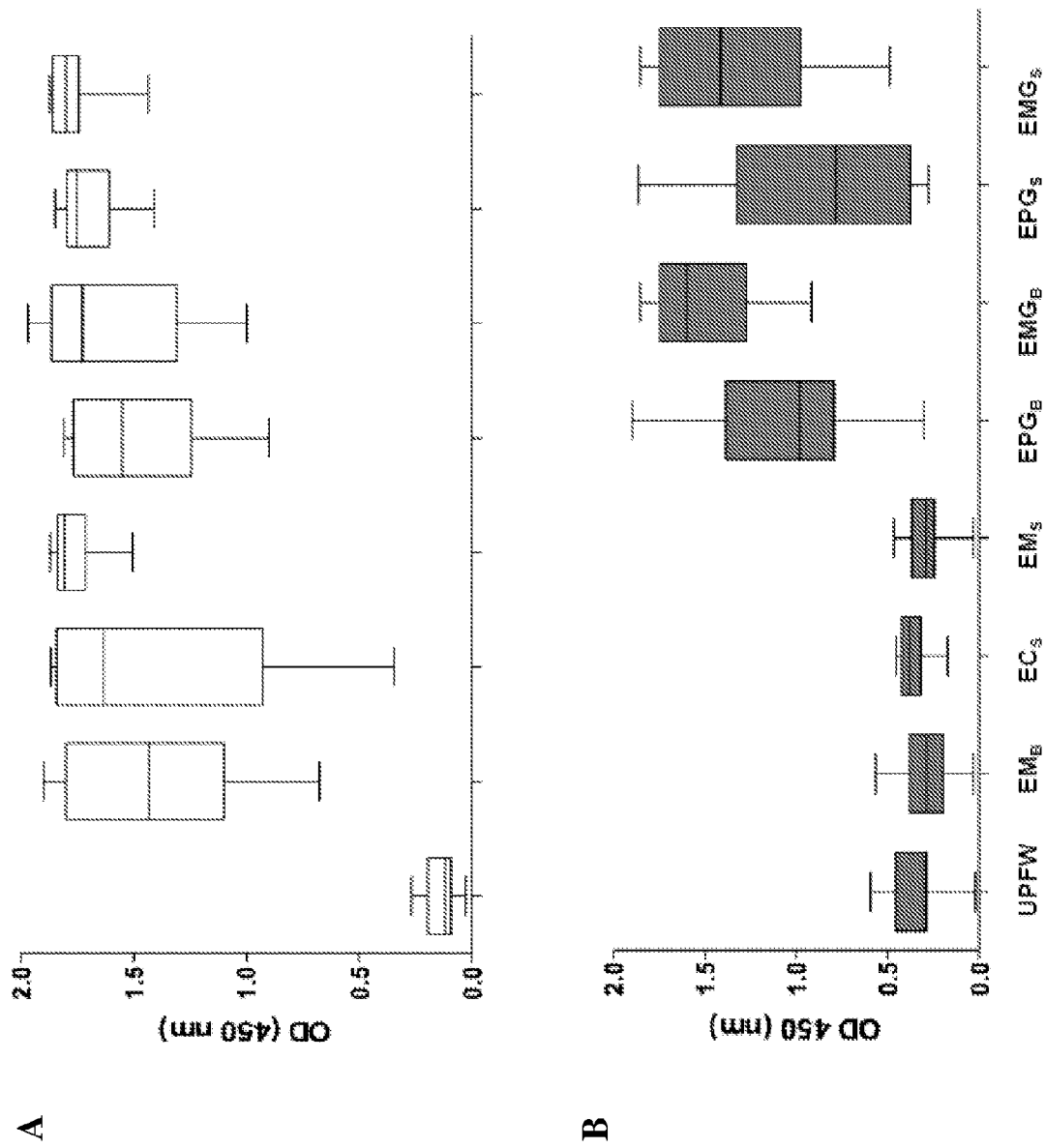
FIG. 5 shows pregnancy-specificity and parity-dependency of plasma IgG reactivity to VAR2CSA NTS-DBL1x-Id1-DBL2x recombinant protein. ELISA was carried out on plates coated with 0.5 mg/mL of PfAMA1 (A) and recombinant NTS-DBL1x-Id1-DBL2x domain of VAR2CSA (B). The IgG plasma levels are expressed as optical densities (OD) and are shown for unexposed pregnant French women (UPFW, n=20), malaria-exposed Beninese men (EMB, n=20), malaria-exposed Senegalese children (ECS, n=20), malaria-exposed Senegalese men (EMS, n=20), and two malaria-exposed pregnant women areas: Benin [primigravidae, (EPGB, n=20) and multigravidae (EMGB, n=20)] and Senegal [primigravidae, (EPG, n=20) and multigravidae (EMG, n=20)].

The recombinant NTS-DBL1x-Id1-DBL2x produced in insect cells was recognized by plasma from malaria exposed pregnant women from Benin and Senegal in a parity-dependent manner (FIG. 5). This NTS-DBL1x-Id1-DBL2x was used in competition ELISA to analyze target epitopes among antibodies induced in animals by plasmid DNA immunization and protein immunization, as well as the naturally acquired antibodies against the NTS-DBL1x-Id1-DBL2x region of VAR2CSA in pregnant women. A mutual inhibition pattern was observed in the ability of all three antisera to recognize the recombinant NTS-DBL1x-Id1-DBL2x protein. The inhibition pattern between sera from DNA immunizations and protein immunizations was concentration-dependent (FIG. 4B). A similar inhibition was observed when antibodies in a human plasma pool from exposed multigravidae competed with specific anti-sera from rabbits (FIG. 4C).

The Naturally Acquired Human IgG Against VARCSA NTS-DBL1x-Id1-DBL2x Inhibit Adhesion of Infected Erythrocytes to CSA.

Figure 6:
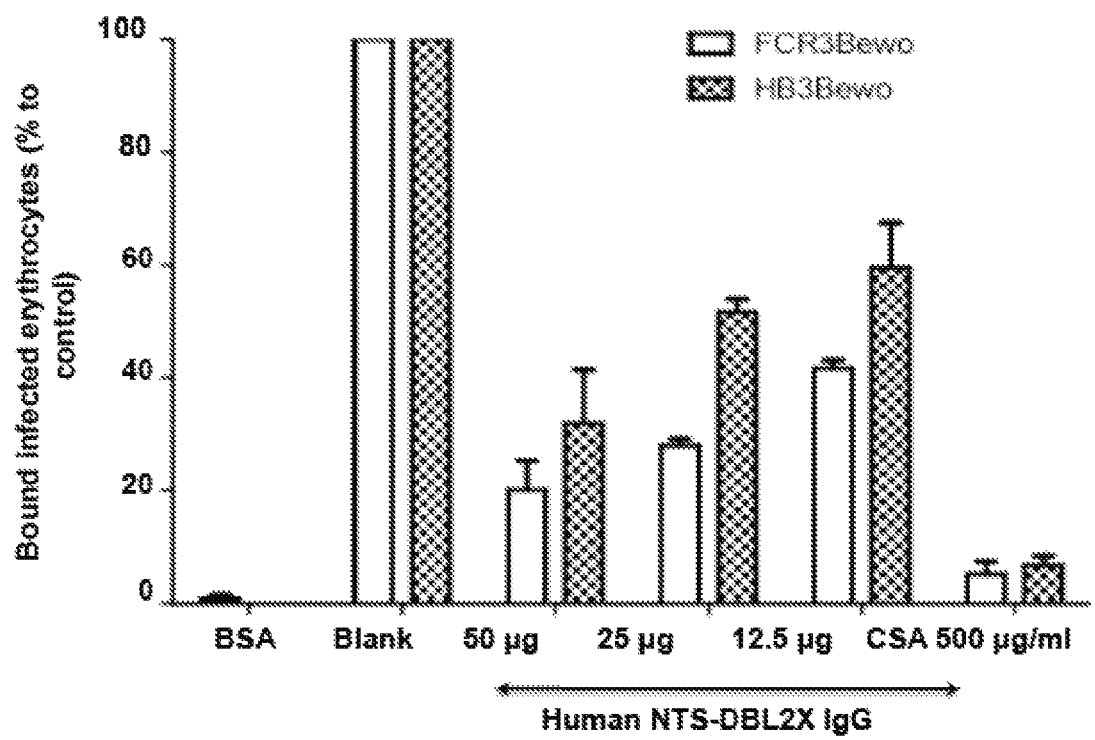
FIG. 6 shows that naturally acquired IgGs against VAR2CSA NTS-DBL1x-Id1-DBL2x target strain-transcendent anti-adhesion epitopes. Specific human IgGs to NTS-DBL1x-Id1-DBL2x were affinity-purified from a pool of plasma from 10 multigravid women that previously showed anti-adhesion capacities. The FCR3-BeWo and HB3-BeWo infected erythrocytes were incubated with different concentrations (12.5, 25 or 50 µg/mL) of the purified human anti-NTS-DBL1x-Id1-DBL2x IgG and the activity was compared to binding without competitor or soluble competing CSA. None of the infected erythrocytes bound to BSA.

Plasma samples from women included in the STOPPAM project are routinely analyzed for anti-adhesion capacity on the FCR3-BeWo parasite lines. The recombinant NTS-DBL1x-Id1-DBL2x protein was used to affinity-purity IgG from plasma of malaria-exposed Beninese pregnant women (selected for having a high anti-adhesion activity on CSA-binding parasite lines). Interestingly, naturally-acquired antibodies targeting the NTS-DBL1x-Id1-DBL2x of VAR2CSA demonstrated anti-adhesion activity. This activity was shown both on FCR3-BeWo and HB3-HeWo parasite lines, with a clear concentration-dependent effect of purified IgG (FIG. 6). This is the first time that naturally acquired antibodies to a specific VAR2CSA region have been shown to inhibit *P. falciparum* infected erythrocytes binding to CSA.

Discussion

Molecular details of the interaction of the *P. falciparum* ligand VAR2CSA with the placental receptor CSA are currently not well delineated, but recent studies suggest that the binding site depends on a higher-order architecture in which DBL domains and the interdomain regions of VAR2CSA fold together to form a ligand-binding pocket (Khunrae et al., J. Mol. Biol., 2010, 397: 826-834; Dahlback et al., Trends Parasitol., 2010, 26: 230-235). However, polyclonal antibodies induced by immunization with the recombinant extracellular part of VAR2CSA highly inhibit binding of infected erythrocytes to CSA in vitro (Khunrae et al., J. Mol. Biol., 2010, 397: 826-834). This suggests that protective immunity to placental malaria acquired over a few pregnancies in areas of intense *P. falciparum* transmission that correlates with levels of anti-adhesion antibodies (Duffy et al., Infect. Immun., 2003, 71: 6620-6623) is mostly mediated by anti-VAR2CSA IgGs. Nevertheless, a recent work reports that immunization with full-length VAR2CSA did not induce potent cross-inhibitory antibodies (Avril et al., PLoS One, 2011, 7:6(2): e16622).

Although antibody response may directly inhibit infected erythrocytes adhesion placenta, it also might be implicated in opsonization (Keen et al., PLoS Med, 2007, 4(5):e181; Feng et al., J. Infect. Dis., 2009, 15:200(2):299-306).

VAR2CSA thus appears as an important candidate for vaccine development. However sequence analyses among parasites have shown that it is a polymorphic protein composed of alternating areas of substantial interclonal polymorphism (Bockhorst et al., Mol. Biochem. Parasitol., 2007, 155: 103-112; Fernandez et al., Malaria J., 2008, 7: 170). The rationale for developing an effective VAR2SA-based vaccine against placental malaria thus requires definition of VAR2CSA areas containing functionally important epitopes that transcend this interclonal diversity. In the present study, full-length and truncated VAR2CSA constructs were tested for their ability to induce adhesion inhibitory antibodies.

The DNA vaccine technology that has proven efficient on various pathogens and tumor antigens (Kutzler et al., Nat. Rev. Genet., 2008, 9; 776-788), was successfully used here with the *P. falciparum* var2csa gene. The resurgence in interest for such concept observed in the last few years is due to several technical improvements such as codon optimization strategies, novel formulations and more effective delivery approaches. The delivery of electrical pulses after intramuscular plasmid DNA infection particularly enhanced DNA uptake and resulted in a stronger and more specific humoral response when the antigen was fused to a leader sequence (Trollet et al., Infect. Immun., 2009, 77: 2221-2229). Several clinical trial based on this approach are currently ongoing in the fields of cancer and infectious diseases. One of these trials that started in July 2010 targets *Plasmodium falciparum* malaria.

In the present study, a strong immune response was obtained both in mice and in rabbits vaccinated with VAR2CSA genetic fragments that were fused to mEPO leader sequence. Interestingly, all antibodies induced were able to recognize the native protein expressed on the surface of erythrocytes infected with the homologous FCR3 parasite line. In line with data previous reported by Khunrae et al. (Khunrae et al., J. Mol. Biol., 2010, 397: 826-834), the plasmid encoding the full-length extracellular part of the protein induced a robust humoral response that completely blocked infected erythrocytes binding to CSPG. However, the major finding of this study is that a shorter construct of the N-terminal moiety of VAR2CSA corresponding to NTS-DBL1x-Id1-DBL2x was able to induce high potency antibodies with similar inhibitory capacity as those elicited against the full-length VAR2CSA. Moreover, competition ELISA analysis revealed that antibodies raised by experimental immunization (plasmid DNA or purified recombinant protein) or those naturally acquired by pregnant women to this particular region of VAR2CSA predominantly target similar epitopes. This result is in line with others that reported that pregnant women do acquire cross-reactive antibodies (Elliott et al., Infect. Immun., 2005, 73(5): 5903-5907; Beeson et al., J. Infect. Dis., 2006, 193(5): 721-730). This suggests that vaccination may reproduce, at least partially, natural acquired immunity against placental malaria.

Recombinant NTS-DBL1x-Id1-DBL2x expressed in insect cells was specifically recognized by sera from malaria-exposed women in a parity-dependent manner supporting the fact that this recombinant protein exhibits important targets of the immune response against VAR2CSA. Murine polyclonal antibodies raised against this construct from the FCR3 parasite strain stained the surface of most isolates from pregnant women of Benin. Remarkably, antibodies raised against a single variant of NTS-DBL1x-Id1-DBL2x showed consistent inhibitory activity against several isolates originating from pregnant women. Actually, the binding of infected erythrocytes to CSPG/CSA of 12 out of the 15 pregnant women isolates tested was inhibited by more than 50%. This highlights the existence of functionally important epitopes within this region of VAR2CSA that are shared by most placenta-sequestering *P. falciparum* isolates. However, all isolates were not inhibited as a probable consequence of antigenic polymorphism. Possible mechanisms of action include that anti-NTS-DBL1x-Id1-DBL2x antibodies inhibit infected erythrocytes adhesion to CSPG/CSA by blocking a single unique CSA binding-site exhibited in the quaternary structure of VAR2CSA, or by modifying the assembly of such high ordered structure mediating the binding of native VAR2CSA to CSA (Nielsen et al., Infect. Immun., 2009, 77: 2482-2487).

The results presented here clearly indicate that antibody recognition of just a few VAR2CSA variants containing key epitopes might be sufficient to markedly affect the binding of VAR2CSA-expressing infected erythrocytes to CSA.

Of particular interest, maternal antibodies purified with the recombinant NTS-DBL1x-Id1-DBL2x reacted with both BeWo-selected FCR3 and HB3 strains, and showed high inhibitory activity on these two distinct parasite lines. This indicates that the inhibitory properties of anti-VAR2CSA antibodies observed in the current study are of biological significance in the acquired immune protection to placental malaria. It was recently shown that some VAR2CSA-specific human monoclonal IgGs from *P. falciparum*-exposed women can exhibit some moderate degree of adhesion inhibition that increases with their combination (Barfod et al., J. Immunol., 2010, 185: 7553-7561). To the best of the inventor's knowledge, the present study clearly shows functional evidence on a specific area of VAR2CSA that is a target of significant naturally acquired anti-adhesion antibodies.

In conclusion, genetic immunization by intramuscular plasmid electrotransfer represents a general technology for fast and efficient screening of immunogenic domains within large proteins of which optimal production as recombinant proteins are technically demanding. This work showed that a truncated N-terminal region of VAR2CSA was a major target of anti-adhesion immune response in placental malaria, and therefore an attractive vaccine target. Further studies are required to ascertain the impact of sequence variation within this particular VAR2CSA region to its potential for cross-reactivity.

Example 2

Identification, Production and Analysis of Id1-DBL2x

In the study presented in this section, the inventors have investigated the possibility of identifying functionally important VAR2CSA regions, in particular functionally important regions of the NTS-DBL1x-Id-DBL2x portion of VAR2CSA, which can induce IgG with high adhesion inhibitory capacity.

Materials and Methods

Figure 8:
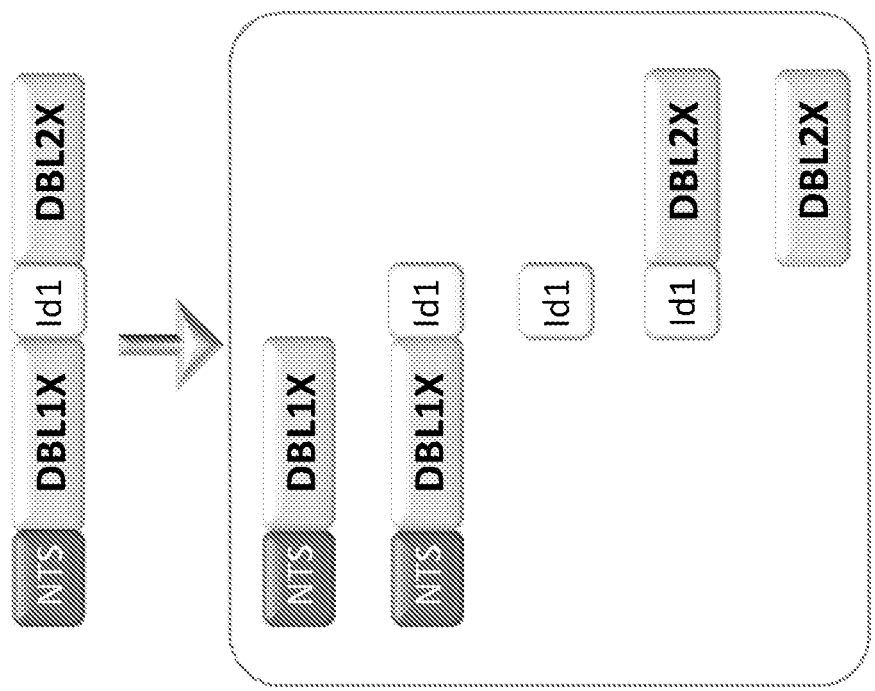
FIG. 8 is a scheme showing the different portions of the NTS-DBL1x-Id1-DBL2x that have been tested to further refine the important protective epitope region.

To further refine the important protective epitope region, five additional constructs were built based upon the NTS-DBL1x-DBL2x sequence, encoding NTS-DBL1x, NTS-DBL1x-Id1, Id1, Id1-DBL2x, and DBL2x, as shown in FIG. 8. DNA sequences encoding the subfragments of NTS-DBL1x-DBL2x were clones into a pVAX1 vector backbone (Invitrogen) as already described (Trollet et al., Infect. Immun., 2009, 77: 2221-2229). Mice were immunized with these constructs as described above in Example 1.

Results

Figure 7:
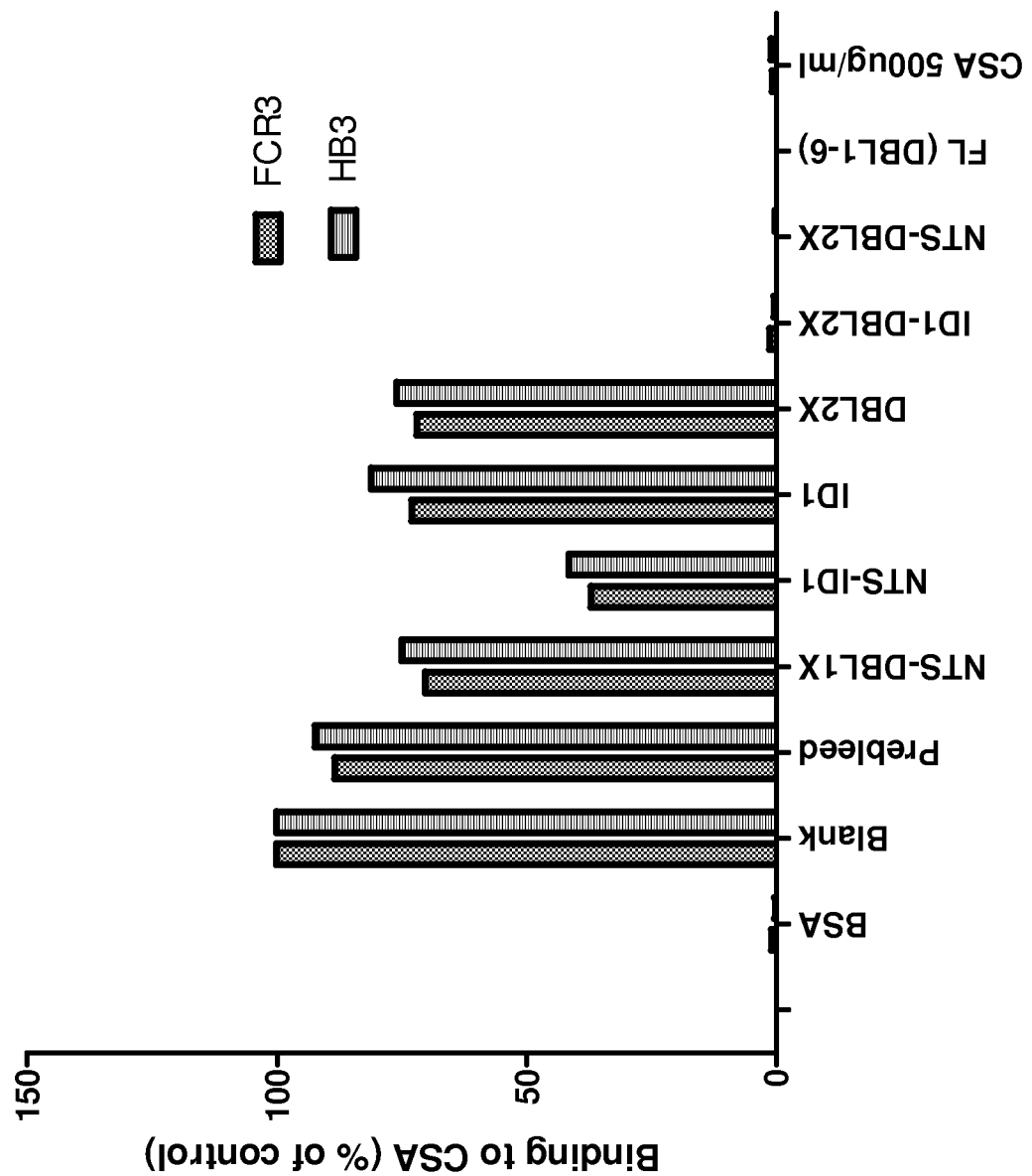
FIG. 7 shows the functional capacity of the antibodies targeting different portions of the N-terminal region of VAR2CSA. The graph shows the ability of immune serum to specific constructs to inhibit binding to CSA by VAR2CSA expressing FCR3 and HB3 infected erythrocytes.

The results obtained are presented on FIG. 7. All constructs but the Id1 successfully raised an immune response. The NTS-DBL1x, NTS-DBL1x-Id1 and Id1-DBL2x fragments raised high titer immune response, comparable to that obtained with the full extracellular part NTS-DBL1x-6ε. Among these constructs, binding inhibitory capacity of infected erythrocytes to CSA was not found with NTS-DBL1x antiserums, highlighting that the VAR2CSA minimal construct inducing anti-adhesion antibodies is beyond the DBL1x domain. However, the construct made of Id1 alone did not induce significant immune response. This refined experiment allowed the identification of Id1-DBL2x (corresponding to the sequence from amino acid 392 to amino acid 866 of VAR2CSA—i.e., SEQ ID NO: 2) as the minimal region concentrating the main anti-adhesion epitopes.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A fusion protein consisting of an isolated polypeptide fused to a fusion partner, wherein the polypeptide consists of the amino acid sequent set forth in SEQ ID NO: 1 or the amino acid sequence set forth in SEQ ID NO: 2.

2. The fusion protein according to claim 1, wherein the fusion partner is selected from the group consisting of maltose binding protein, signal sequence of the maltose binding protein, poly-histidine tag, S-Tag, glutathione-S-transferase, thioredoxin, β-galactosidase, streptavidin, dihydrofolate reductase, pelB signal sequence, ompA signal sequence, signal sequence of alkaline phosphatase, green fluorescent protein (GFP), human growth hormone, interleukin-2 (IL-2), granulocyte macrophage colony stimulating factor (GM-CSF), granulocyte colony stimulating factor (G-CSF), calcitonin, interferon-beta, interferon-alpha, glucagon like peptide 1 (GLP-1), glucagon like peptide 2 (GLP-2), parathyroid hormone PTH(1-34), parathyroid hormone PTH(1-84), butyrylcholinesterase, glucocerebrosidase (GBA), and exendin-4.

3. An immunogenic composition comprising the fusion protein according to claim 1 and at least one pharmaceutically acceptable carrier or excipient.

4. The immunogenic composition according to claim 3, further comprising an adjuvant.

5. An immunogenic composition comprising the fusion protein according to claim 2 and at least one pharmaceutically acceptable carrier or excipient.

6. The immunogenic composition according to claim 5, further comprising an adjuvant.

7. A method of inducing an immune response against *Plasmodium falciparum* in a female human being, comprising administering to said female human being an effective amount of the immunogenic composition of claim 4.

8. The method according to claim 7, wherein the female human being is a prepubertal girl, a postpupertal girl, or a primigravidae woman.

9. A method of inducing an immune response against *Plasmodium falciparum* in a female human being, comprising administering to said female human being an effective amount of the immunogenic composition of claim 6.

10. The method according to claim 9, wherein the female human being is a prepubertal girl, a postpupertal girl, or a primigravidae woman.

* * * * *

```
                           SEQUENCE LISTING

<160> NUMBER OF SEQ ID NOS: 2

<210> SEQ ID NO 1
<211> LENGTH: 858
<212> TYPE: PRT
<213> ORGANISM: Plasmodium falciparum

<400> SEQUENCE: 1

Asn Lys Ile Glu Ala Tyr Leu Gly Ala Lys Ser Asp Asp Ser Lys Ile
1               5                   10                  15

Asp Gln Ser Leu Lys Ala Asp Pro Ser Glu Val Gln Tyr Tyr Gly Ser
            20                  25                  30

Gly Gly Asp Gly Tyr Tyr Leu Arg Lys Asn Ile Cys Lys Ile Thr Val
        35                  40                  45

Asn His Ser Asp Ser Gly Thr Asn Asp Pro Cys Asp Arg Ile Pro Pro
    50                  55                  60

Pro Tyr Gly Asp Asn Asp Gln Trp Lys Cys Ala Ile Ile Leu Ser Lys
65                  70                  75                  80

Val Ser Glu Lys Pro Glu Asn Val Phe Val Pro Pro Arg Arg Gln Arg
                85                  90                  95

Met Cys Ile Asn Asn Leu Glu Lys Leu Asn Val Asp Lys Ile Arg Asp
            100                 105                 110

Lys His Ala Phe Leu Ala Asp Val Leu Leu Thr Ala Arg Asn Glu Gly
        115                 120                 125

Glu Arg Ile Val Gln Asn His Pro Asp Thr Asn Ser Ser Asn Val Cys
    130                 135                 140

Asn Ala Leu Glu Arg Ser Phe Ala Asp Ile Ala Asp Ile Ile Arg Gly
145                 150                 155                 160

Thr Asp Leu Trp Lys Gly Thr Asn Ser Asn Leu Glu Gln Asn Leu Lys
                165                 170                 175

Gln Met Phe Ala Lys Ile Arg Glu Asn Asp Lys Val Leu Gln Asp Lys
            180                 185                 190

Tyr Pro Lys Asp Gln Asn Tyr Arg Lys Leu Arg Glu Asp Trp Trp Asn
        195                 200                 205

Ala Asn Arg Gln Lys Val Trp Glu Val Ile Thr Cys Gly Ala Arg Ser
    210                 215                 220

Asn Asp Leu Leu Ile Lys Arg Gly Trp Arg Thr Ser Gly Lys Ser Asn
225                 230                 235                 240

Gly Asp Asn Lys Leu Glu Leu Cys Arg Lys Cys Gly His Tyr Glu Glu
                245                 250                 255

Lys Val Pro Thr Lys Leu Asp Tyr Val Pro Gln Phe Leu Arg Trp Leu
            260                 265                 270

Thr Glu Trp Ile Glu Asp Phe Tyr Arg Glu Lys Gln Asn Leu Ile Asp
        275                 280                 285

Asp Met Glu Arg His Arg Glu Glu Cys Thr Ser Glu Asp His Lys Ser
    290                 295                 300

Lys Glu Gly Thr Ser Tyr Cys Ser Thr Cys Lys Asp Lys Cys Lys Lys
305                 310                 315                 320

Tyr Cys Glu Cys Val Lys Lys Trp Lys Ser Glu Trp Glu Asn Gln Lys
                325                 330                 335
```

-continued

```
Asn Lys Tyr Thr Glu Leu Tyr Gln Gln Asn Lys Asn Glu Thr Ser Gln
            340                 345                 350
Lys Asn Thr Ser Arg Tyr Asp Asp Tyr Val Lys Asp Phe Phe Lys Lys
        355                 360                 365
Leu Glu Ala Asn Tyr Ser Ser Leu Glu Asn Tyr Ile Lys Gly Asp Pro
    370                 375                 380
Tyr Phe Ala Glu Tyr Ala Thr Lys Leu Ser Phe Ile Leu Asn Ser Ser
385                 390                 395                 400
Asp Ala Asn Asn Pro Ser Glu Lys Ile Gln Lys Asn Asn Asp Glu Val
                405                 410                 415
Cys Asn Cys Asn Glu Ser Gly Ile Ala Ser Val Glu Gln Gln Ile
            420                 425                 430
Ser Asp Pro Ser Ser Lys Thr Cys Ile Thr His Ser Ser Ile Lys Ala
        435                 440                 445
Asn Lys Lys Lys Val Cys Lys His Val Lys Leu Gly Val Arg Glu Asn
    450                 455                 460
Asp Lys Asp Leu Arg Val Cys Val Ile Glu His Thr Ser Leu Ser Gly
465                 470                 475                 480
Val Glu Asn Cys Cys Cys Gln Asp Phe Leu Arg Ile Leu Gln Glu Asn
                485                 490                 495
Cys Ser Asp Asn Lys Ser Gly Ser Ser Asn Gly Ser Cys Asn Asn
            500                 505                 510
Lys Asn Gln Glu Ala Cys Glu Lys Asn Leu Glu Lys Val Leu Ala Ser
        515                 520                 525
Leu Thr Asn Cys Tyr Lys Cys Asp Lys Cys Lys Ser Glu Gln Ser Lys
    530                 535                 540
Lys Asn Asn Lys Asn Trp Ile Trp Lys Ser Ser Gly Lys Glu Gly
545                 550                 555                 560
Gly Leu Gln Lys Glu Tyr Ala Asn Thr Ile Gly Leu Pro Pro Arg Thr
                565                 570                 575
Gln Ser Leu Cys Leu Val Val Cys Leu Asp Glu Lys Gly Lys Lys Thr
            580                 585                 590
Gln Glu Leu Lys Asn Ile Arg Thr Asn Ser Glu Leu Leu Lys Glu Trp
        595                 600                 605
Ile Ile Ala Ala Phe His Glu Gly Lys Asn Leu Lys Pro Ser His Glu
    610                 615                 620
Lys Lys Asn Asp Asp Asn Gly Lys Lys Leu Cys Lys Ala Leu Glu Tyr
625                 630                 635                 640
Ser Phe Ala Asp Tyr Gly Asp Leu Ile Lys Gly Thr Ser Ile Trp Asp
                645                 650                 655
Asn Glu Tyr Thr Lys Asp Leu Glu Leu Asn Leu Gln Leu Gln Lys Ile
            660                 665                 670
Phe Gly Lys Leu Phe Arg Lys Tyr Ile Lys Lys Asn Asn Thr Ala Glu
        675                 680                 685
Gln Asp Thr Ser Tyr Ser Ser Leu Asp Glu Leu Arg Glu Ser Trp Trp
    690                 695                 700
Asn Thr Asn Lys Lys Tyr Ile Trp Leu Ala Met Lys His Gly Ala Gly
705                 710                 715                 720
Met Asn Ser Thr Thr Cys Cys Gly Asp Gly Ser Val Thr Gly Ser Gly
                725                 730                 735
Ser Ser Cys Asp Asp Ile Pro Thr Ile Asp Leu Ile Pro Gln Tyr Leu
            740                 745                 750
Arg Phe Leu Gln Glu Trp Val Glu His Phe Cys Lys Gln Arg Gln Glu
```

-continued

```
                755                 760                 765
Lys Val Lys Pro Val Ile Glu Asn Cys Lys Ser Cys Lys Glu Ser Gly
            770                 775                 780
Gly Thr Cys Asn Gly Glu Cys Lys Thr Glu Cys Lys Asn Lys Cys Glu
785                 790                 795                 800
Val Tyr Lys Lys Phe Ile Glu Asp Cys Lys Gly Asp Gly Thr Ala
                805                 810                 815
Gly Ser Ser Trp Val Lys Arg Trp Asp Gln Ile Tyr Lys Arg Tyr Ser
            820                 825                 830
Lys Tyr Ile Glu Asp Ala Lys Arg Asn Arg Lys Ala Gly Thr Lys Asn
            835                 840                 845
Cys Gly Pro Ser Ser Thr Thr Asn Ala Ala
            850                 855
```

<210> SEQ ID NO 2
<211> LENGTH: 475
<212> TYPE: PRT
<213> ORGANISM: Plasmodium falciparum

<400> SEQUENCE: 2

```
Pro Tyr Phe Ala Glu Tyr Ala Thr Lys Leu Ser Phe Ile Leu Asn Pro
1               5                   10                  15
Ser Asp Ala Asn Asn Pro Ser Gly Glu Thr Ala Asn His Asn Asp Glu
            20                  25                  30
Ala Cys Asn Cys Asn Glu Ser Gly Ile Ser Ser Val Gly Gln Ala Gln
        35                  40                  45
Thr Ser Gly Pro Ser Ser Asn Lys Thr Cys Ile Thr His Ser Ser Ile
    50                  55                  60
Lys Thr Asn Lys Lys Glu Cys Lys Asp Val Lys Leu Gly Val Arg
65                  70                  75                  80
Glu Asn Asp Lys Asp Leu Lys Ile Cys Val Ile Glu Asp Thr Ser Leu
                85                  90                  95
Ser Gly Val Asp Asn Cys Cys Cys Gln Asp Leu Leu Gly Ile Leu Gln
            100                 105                 110
Glu Asn Cys Ser Asp Asn Lys Arg Gly Ser Ser Ser Asn Asp Ser Cys
        115                 120                 125
Asp Asn Lys Asn Gln Asp Glu Cys Gln Lys Lys Leu Glu Lys Val Phe
    130                 135                 140
Ala Ser Leu Thr Asn Gly Tyr Lys Cys Asp Lys Cys Lys Ser Gly Thr
145                 150                 155                 160
Ser Arg Ser Lys Lys Trp Ile Trp Lys Ser Ser Gly Asn Glu
                165                 170                 175
Glu Gly Leu Gln Glu Gly Tyr Ala Asn Thr Ile Gly Leu Pro Pro Arg
            180                 185                 190
Thr Gln Ser Leu Tyr Leu Gly Asn Leu Pro Lys Leu Glu Asn Val Cys
        195                 200                 205
Glu Asp Val Lys Asp Ile Asn Phe Asp Thr Lys Glu Lys Phe Leu Ala
    210                 215                 220
Gly Cys Leu Ile Val Ser Phe His Glu Gly Lys Asn Leu Lys Lys Arg
225                 230                 235                 240
Tyr Pro Gln Asn Lys Asn Ser Gly Asn Lys Glu Asn Leu Cys Lys Ala
                245                 250                 255
Leu Glu Tyr Ser Phe Ala Asp Tyr Gly Asp Leu Ile Lys Gly Thr Ser
            260                 265                 270
```

-continued

```
Ile Trp Asp Asn Glu Tyr Thr Lys Asp Leu Glu Leu Asn Leu Gln Asn
        275                 280                 285

Asn Phe Gly Lys Leu Phe Gly Lys Tyr Ile Lys Lys Asn Asn Thr Ala
        290                 295                 300

Glu Gln Asp Thr Ser Tyr Ser Ser Leu Asp Glu Leu Arg Glu Ser Trp
305                 310                 315                 320

Trp Asn Thr Asn Lys Lys Tyr Ile Trp Thr Ala Met Lys His Gly Ala
                325                 330                 335

Glu Met Asn Ile Thr Thr Cys Asn Ala Asp Gly Ser Val Thr Gly Ser
                340                 345                 350

Gly Ser Ser Cys Asp Asp Ile Pro Thr Ile Asp Leu Ile Pro Gln Tyr
        355                 360                 365

Leu Arg Phe Leu Gln Glu Trp Val Glu Asn Phe Cys Glu Gln Arg Gln
        370                 375                 380

Ala Lys Val Lys Asp Val Ile Thr Asn Cys Lys Ser Cys Lys Glu Ser
385                 390                 395                 400

Gly Asn Lys Cys Lys Thr Glu Cys Lys Thr Lys Cys Lys Asp Glu Cys
                405                 410                 415

Glu Lys Tyr Lys Lys Phe Ile Glu Ala Cys Gly Thr Ala Gly Gly Gly
                420                 425                 430

Ile Gly Thr Ala Gly Ser Pro Trp Ser Lys Arg Trp Asp Gln Ile Tyr
            435                 440                 445

Lys Arg Tyr Ser Lys His Ile Glu Asp Ala Lys Arg Asn Arg Lys Ala
        450                 455                 460

Gly Thr Lys Asn Cys Gly Thr Ser Ser Thr Thr
465                 470                 475
```